(12) United States Patent
Kallenberger

(10) Patent No.: US 12,343,105 B2
(45) Date of Patent: Jul. 1, 2025

(54) ROBOTIC SURGICAL INSTRUMENTS WITH ROTARY SHAFT POWER TRANSMISSION

(71) Applicant: Cilag GmbH International, Zug (CH)

(72) Inventor: Kris Eren Kallenberger, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1178 days.

(21) Appl. No.: 17/173,278

(22) Filed: Feb. 11, 2021

(65) Prior Publication Data
US 2022/0249187 A1    Aug. 11, 2022

(51) Int. Cl.
| | |
|---|---|
| A61B 34/30 | (2016.01) |
| A61B 17/00 | (2006.01) |
| A61B 34/00 | (2016.01) |
| A61B 17/068 | (2006.01) |
| A61B 17/072 | (2006.01) |
| A61B 17/29 | (2006.01) |
| A61B 17/3201 | (2006.01) |
| A61B 34/37 | (2016.01) |

(52) U.S. Cl.
CPC .............. *A61B 34/74* (2016.02); *A61B 17/00* (2013.01); *A61B 34/30* (2016.02); *A61B 34/70* (2016.02); *A61B 2017/00477* (2013.01); *A61B 17/068* (2013.01); *A61B 2017/07285* (2013.01); *A61B 17/29* (2013.01); *A61B 17/3201* (2013.01); *A61B 34/25* (2016.02); *A61B 2034/301* (2016.02); *A61B 2034/302* (2016.02); *A61B 2034/303* (2016.02); *A61B 34/37* (2016.02); *A61B 2034/715* (2016.02); *A61B 2034/743* (2016.02); *A61B 2217/002* (2013.01); *A61B 2217/005* (2013.01); *A61B 2217/007* (2013.01)

(58) Field of Classification Search
CPC ......... A61B 34/74; A61B 17/00; A61B 34/30; A61B 34/70; A61B 17/29; A61B 17/3201; A61B 34/37; A61B 2034/302; A61B 2034/303; A61B 2034/301; A61B 17/07207; A61B 34/71
See application file for complete search history.

(56) References Cited

U.S. PATENT DOCUMENTS

| | | |
|---|---|---|
| 8,915,842 B2 | 12/2014 | Weisenberg, II et al. |
| 9,446,177 B2 | 9/2016 | Millman et al. |
| 2007/0005002 A1* | 1/2007 | Millman ................ A61B 34/71 604/30 |
| 2017/0105751 A1* | 4/2017 | Hibner .................... B25B 27/02 |
| 2021/0393341 A1* | 12/2021 | Beckman ............... A61B 34/30 |

* cited by examiner

*Primary Examiner* — Nathan R Price
*Assistant Examiner* — Haden Matthew Ritchie
(74) *Attorney, Agent, or Firm* — Vorys, Sater, Seymour and Pease LLP

(57) ABSTRACT

A robotic surgical tool includes a handle and an elongate shaft extendable through the handle and including an outer proximal tube and an inner spline rotatably received within the outer proximal tube. A first actuation system is housed within the handle and operable to rotate the inner spline relative to the outer proximal tube and thereby transfer torque to a proximal or distal end of the shaft. A second actuation system is housed within the handle and operable to drive the outer proximal tube and thereby advance or retract the elongate shaft in z-axis translation through the handle.

20 Claims, 20 Drawing Sheets

ROBOTIC SURGICAL INSTRUMENTS WITH ROTARY SHAFT POWER TRANSMISSION

TECHNICAL FIELD

The systems and methods disclosed herein are directed to robotic surgical tools and, more particularly to, robotic surgical instruments that incorporate a rack-based translation and torque transmission system.

BACKGROUND

Minimally invasive procedures are often preferred over traditional open surgery due to the reduced post-operative recovery time and minimal scarring. In minimally invasive procedures, elongate medical instruments may be inserted into the patient through a small incision or natural orifice to visualize or manipulate tissue for diagnostic or therapeutic purposes. Robotic systems have recently been developed to assist in minimally invasive procedures, where the instruments are controllably manipulated by robot arms to access internal anatomical sites.

During surgery on a patient, it is often desirable to irrigate a surgical site with a fluid, such as water, to clean or clear away blood, tissue, or other items obscuring the vision of a surgeon in the surgical site. Suction or aspiration in the surgical site may also be used to vacuum away blood, tissue, or other items obscuring the vision of the surgeon in the surgical site.

Improvements to robotically-enabled medical systems, such as suction irrigators, will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes a handle, an elongate shaft extendable through the handle and including an outer proximal tube and an inner spline rotatably received within the outer proximal tube, a first actuation system housed within the handle and operable to rotate the inner spline relative to the outer proximal tube and thereby transfer torque to a proximal or distal end of the shaft, and a second actuation system housed within the handle and operable to drive the outer proximal tube and thereby advance or retract the elongate shaft in z-axis translation through the handle. In a further embodiment, the outer proximal tube and the inner spline comprise a proximal shaft assembly and the shaft further includes a distal shaft assembly coupled to the proximal shaft assembly at a connector, the distal shaft assembly comprising an outer distal tube extending distally from the connector, an inner distal tube arranged within the outer distal tube and extending distally from the connector, and a distal tip arranged at a distal end of the shaft and fixed to the outer and inner distal tubes, wherein the inner distal tube defines a first lumen and the inner spline defines a second lumen in fluid communication with the first lumen via the connector to enable fluid flow along a length of the shaft. In another further embodiment, the outer proximal tube is fixed to the connector and the inner spline is rotatably coupled to the connector. In another further embodiment, the connector provides a sealed interface between the first and second lumens. In another further embodiment, the distal tip defines an opening in fluid communication with the first lumen to discharge fluids from the shaft or receive fluids into the shaft. In another further embodiment, the robotic surgical tool further includes a flow control system arranged at a proximal end of the shaft and including a valve operatively coupled to the inner spline such that rotation of the inner spline actuates the valve, a first conduit in fluid communication with the valve to convey a liquid into the first and second lumens to be discharged at the distal tip, and a second conduit in fluid communication with the valve to draw fluids into the first and second lumens at the distal tip. In another further embodiment, the robotic surgical tool further includes a third conduit in fluid communication with the valve to convey a compressed gas into the first and second lumens to be discharged at the distal tip. In another further embodiment, the first actuation system includes a first drive input mounted to the handle and operable to actuate a first drive mechanism engageable with longitudinally-extending gear teeth defined on the inner spline to rotate the inner spline, and wherein the second actuation system includes a second drive input mounted to the handle and operable to actuate a second drive mechanism engageable with a rack provided on the outer proximal tube to advance or retract the shaft in z-axis translation. In another further embodiment, the first actuation system includes a drive gear capable of sliding along the longitudinally-extending gear teeth as the shaft moves in z-axis translation. In another further embodiment, the robotic surgical tool further includes an end effector arranged at a distal end of the shaft, wherein the torque transferred by the inner spline causes actuation of the end effector. In another further embodiment, the inner spline defines a lumen and the robotic surgical tool further comprises an electrical conductor extending within the lumen to the end effector. In another further embodiment, the end effector includes opposing jaws and rotation of the inner spline moves the jaws between open and closed positions.

Embodiments disclosed herein further include a method of operating a robotic surgical tool, the method including arranging a robotic surgical tool adjacent a patient, the robotic surgical tool including an elongate shaft extending through a handle and including an outer proximal tube and an inner spline rotatably received within the outer proximal tube, operating a first actuation system housed within the handle to rotate the inner spline relative to the outer proximal tube and thereby transferring torque to a proximal or distal end of the shaft, and operating a second actuation system housed within the handle to drive the outer proximal tube and thereby advance or retract the elongate shaft in z-axis translation through the handle. In a further embodiment, the outer proximal tube and the inner spline comprise a proximal shaft assembly and the shaft further includes a distal shaft assembly coupled to the proximal shaft assembly at a connector, the distal shaft assembly including an outer distal tube extending distally from the connector, an inner distal tube arranged within the outer distal tube and extending distally from the connector, and a distal tip arranged at a distal end of the shaft and fixed to the outer and inner distal tubes, wherein the inner distal tube defines a first lumen and the inner spline defines a second lumen in fluid communication with the first lumen via the connector, the method further comprising flowing a fluid along a length of the shaft within the first and second lumens. In another further embodiment, the distal tip defines an opening in fluid communication with the first lumen, the method further comprising discharging the fluid from the shaft at the distal tip, and drawing the fluid into the shaft at the distal tip. In another further embodiment, the robotic surgical tool further includes a flow control system arranged at a proximal end of the shaft and including a valve operatively coupled to the inner spline, and wherein operating the second actuation system further comprises actuating the valve to a first position and thereby conveying the fluid into the first and second lumens from to be discharged at the distal tip, and actuating the valve to a second position and thereby drawing the fluid into the first and second lumens at the distal tip. In another further embodiment, operating the first actuation system comprises operating a first drive input mounted to the handle and thereby actuating a first drive mechanism to engage and drive longitudinally-extending gear teeth defined on the inner spline, and operating the second actuation system comprises operating a second drive input mounted to the handle and thereby actuating a second drive mechanism to engage and drive a rack provided on the outer proximal tube to advance or retract the shaft in z-axis translation. In another further embodiment, the first actuation system includes a drive gear engageable with the longitudinally-extending gear teeth, the method further comprising sliding the drive gear along the longitudinally-extending gear teeth as the shaft moves in z-axis translation. In another further embodiment, the robotic surgical tool further comprises an end effector arranged at a distal end of the shaft, and wherein operating the first actuation system comprises transferring the torque to the end effector via rotation of the inner spline, and actuating the end effector with the torque. In another further embodiment, the inner spline defines a lumen and the robotic surgical tool further includes an electrical conductor extending within the lumen to the end effector, the method further comprising providing electrical current to the end effector via the electrical conductor.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
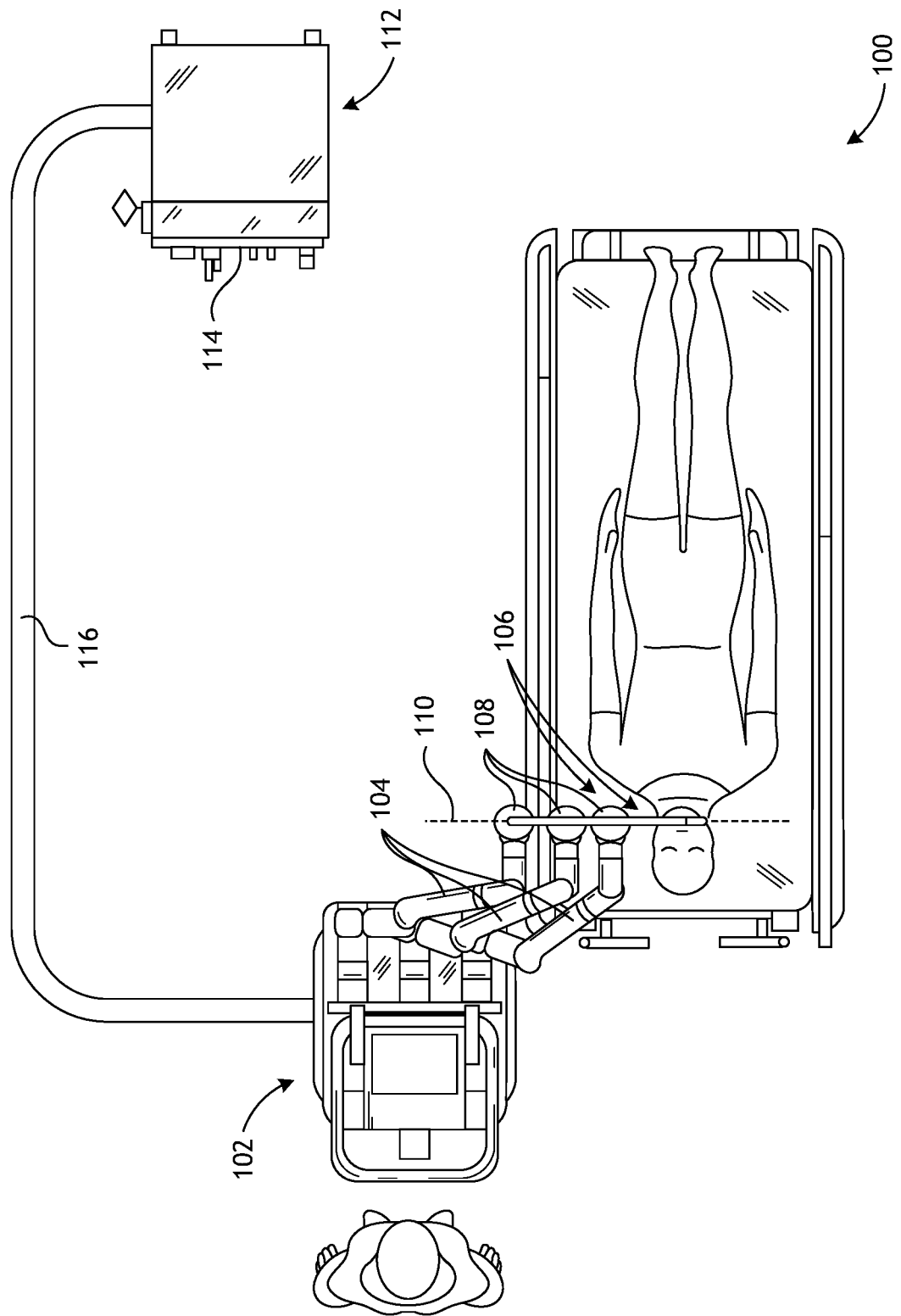
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
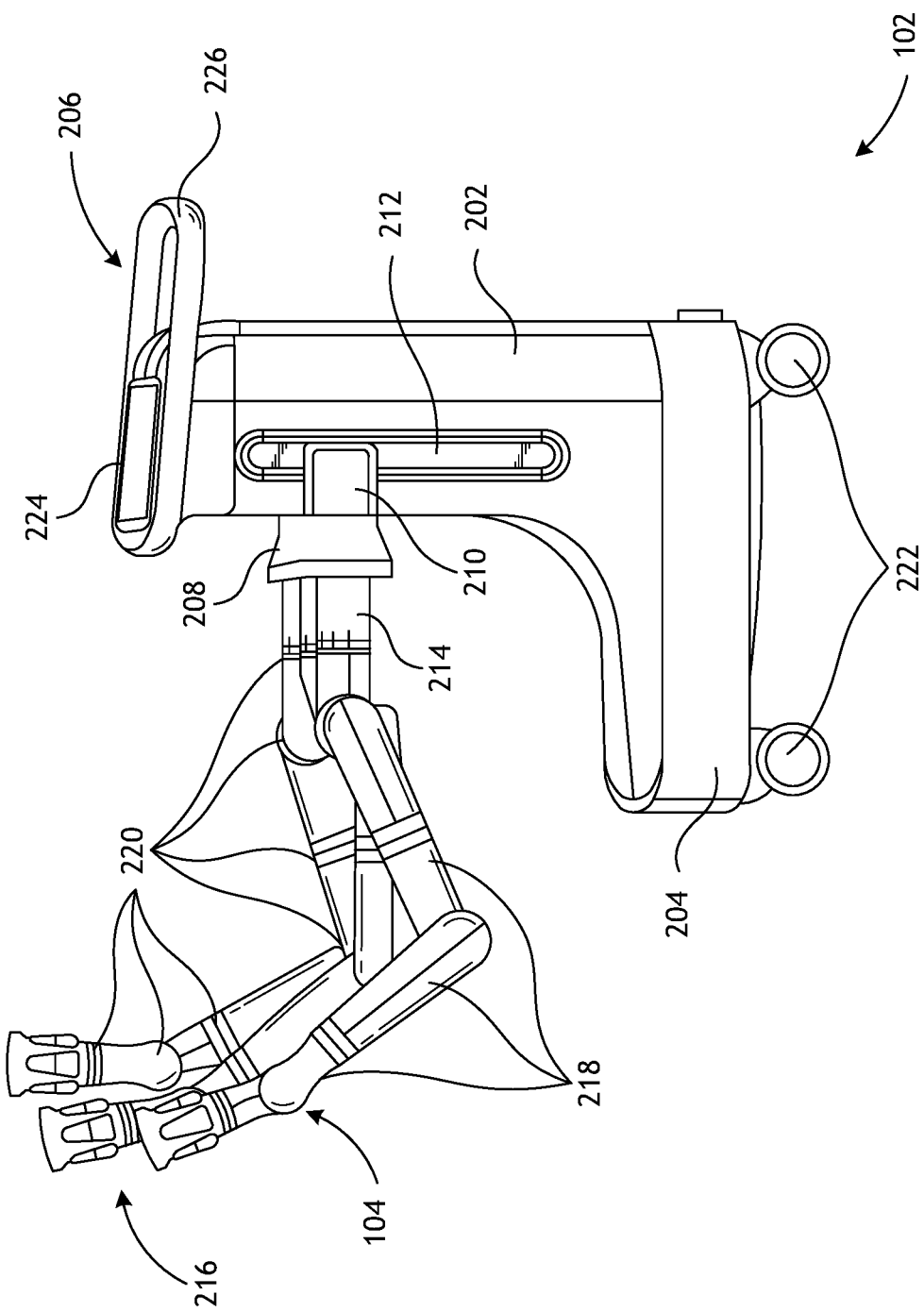
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
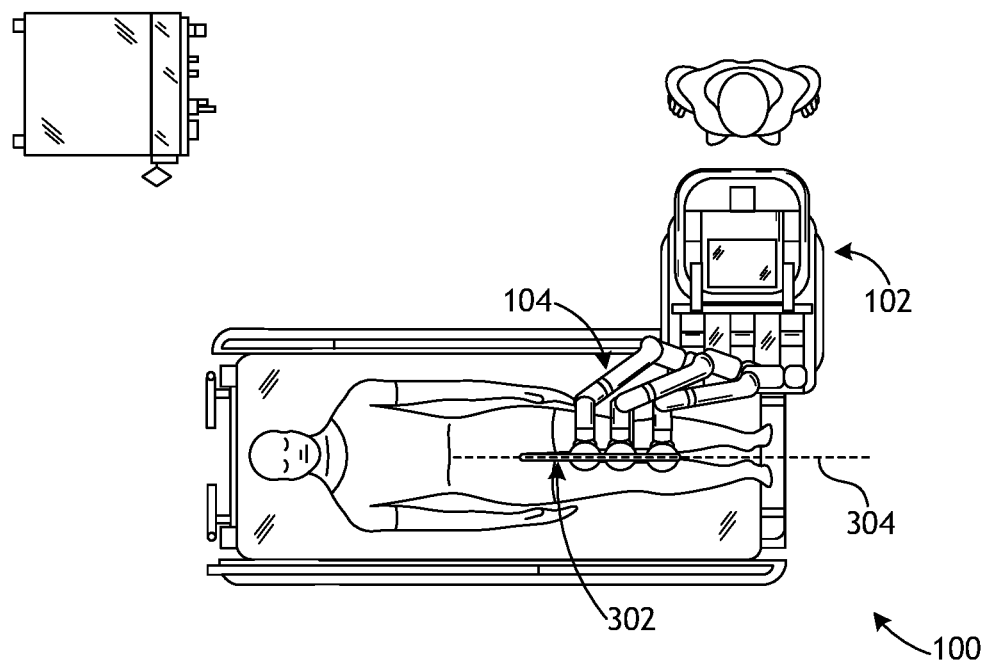
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
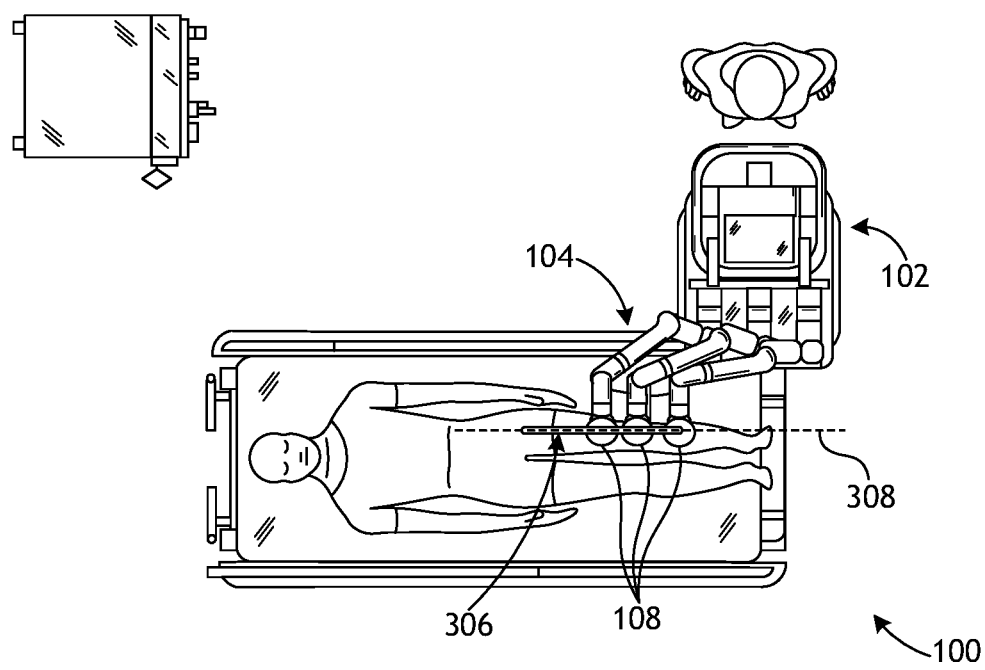
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
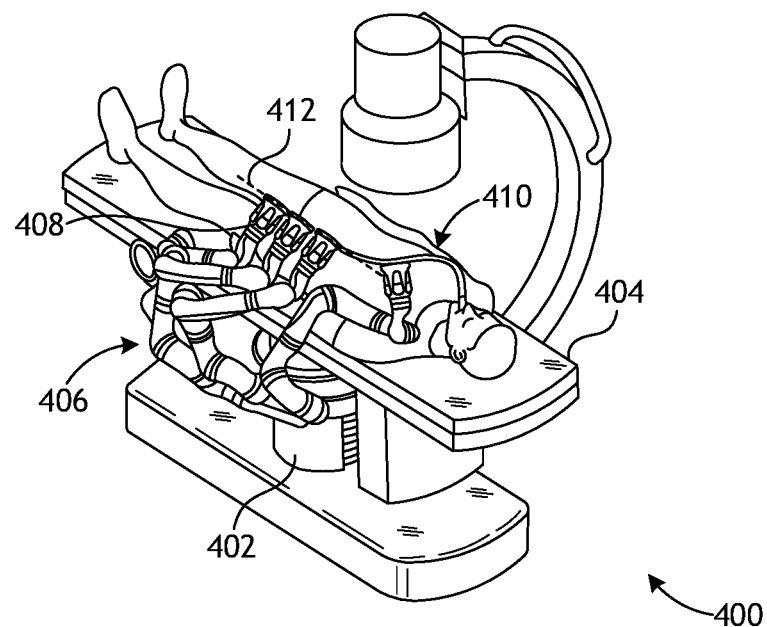
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
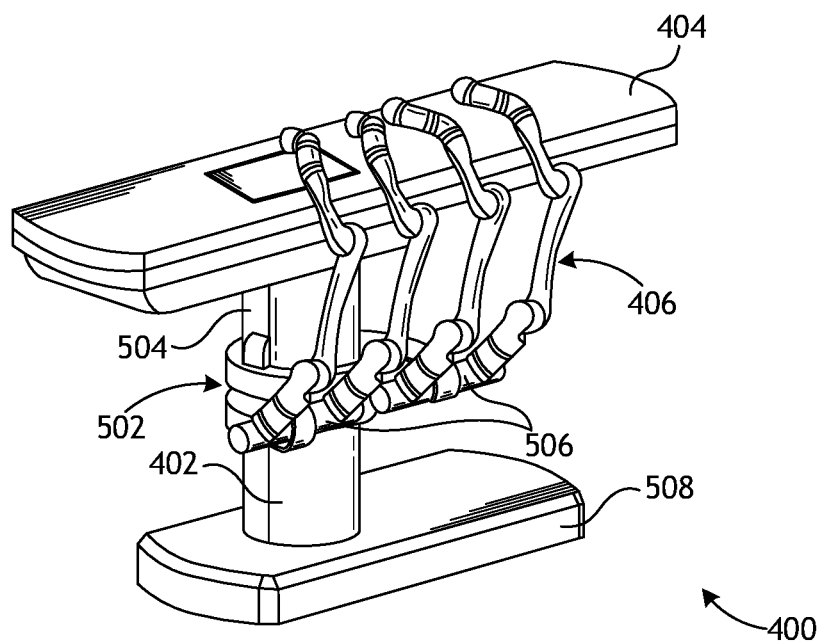
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
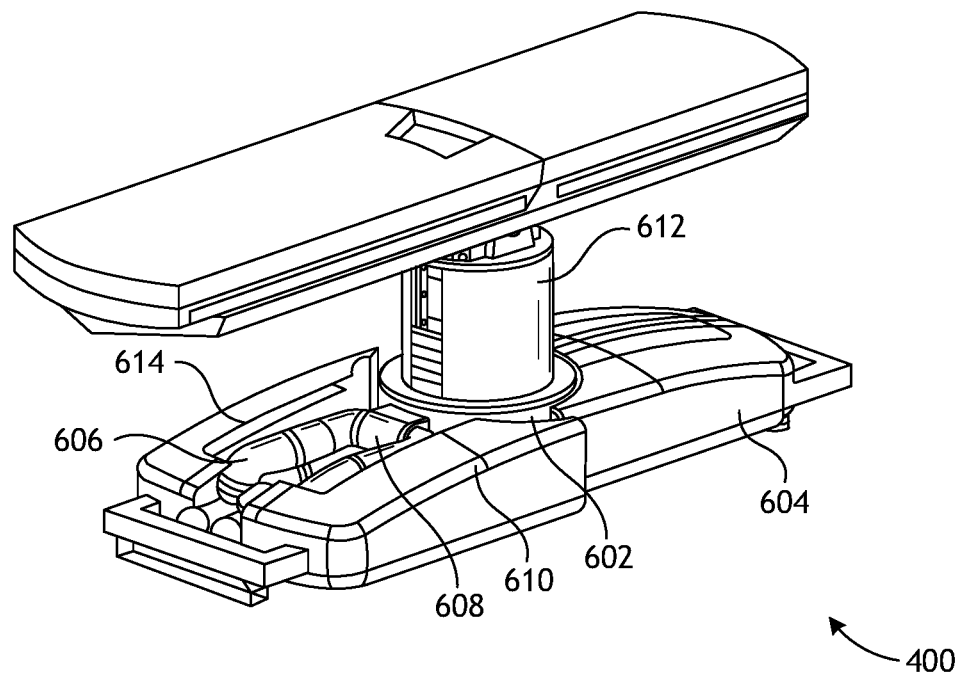
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
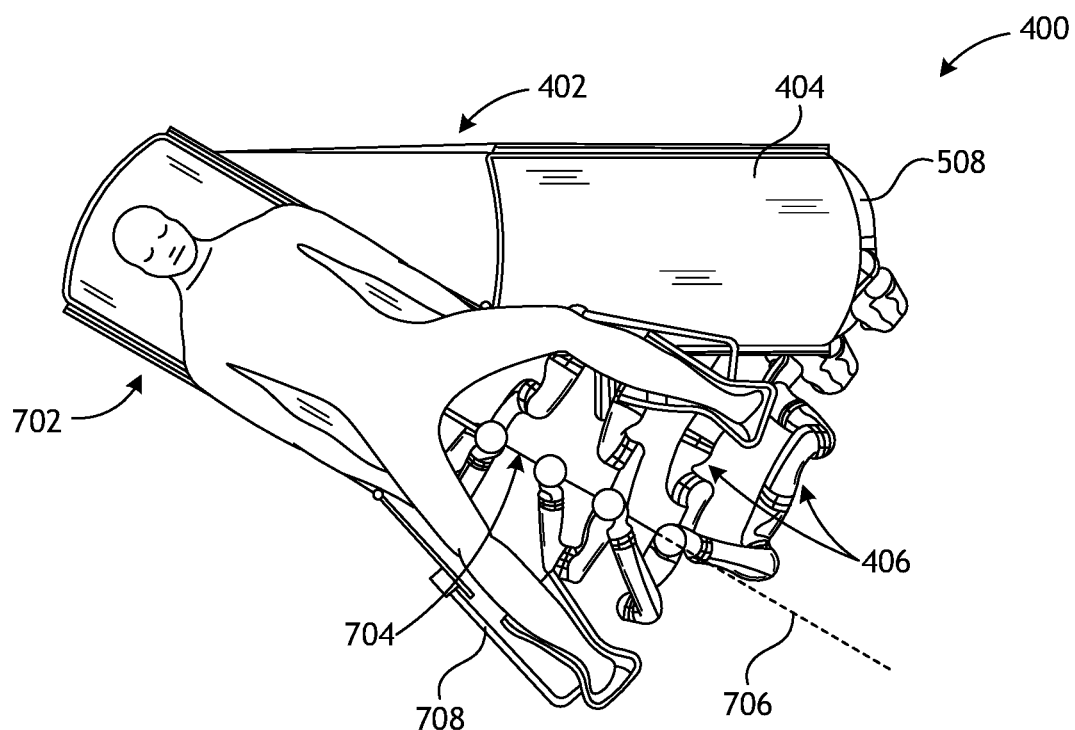
FIG. 7A illustrates an embodiment of a table-based robotic system configured for a ureteroscopy procedure.
Figure 7B:
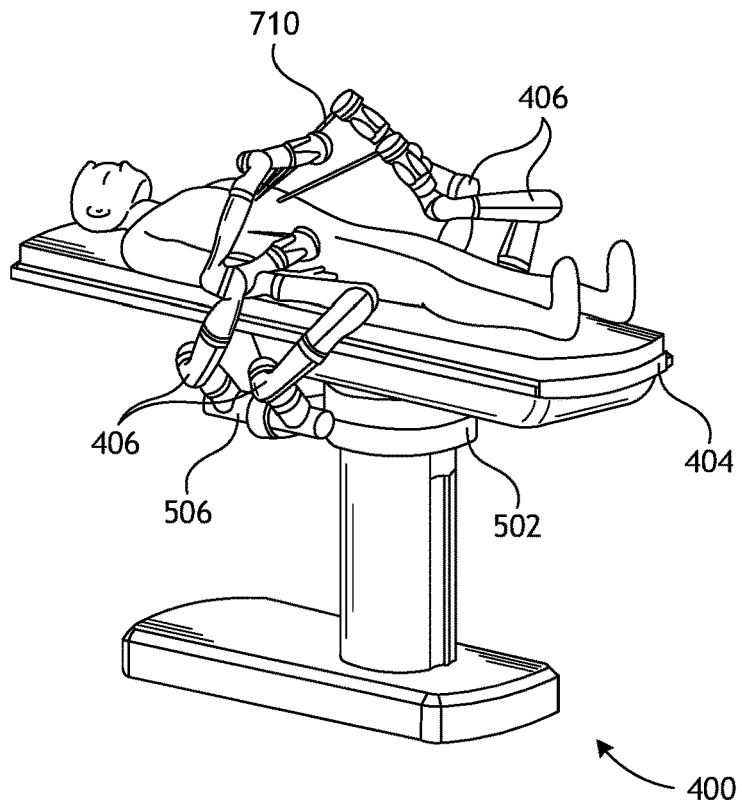
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
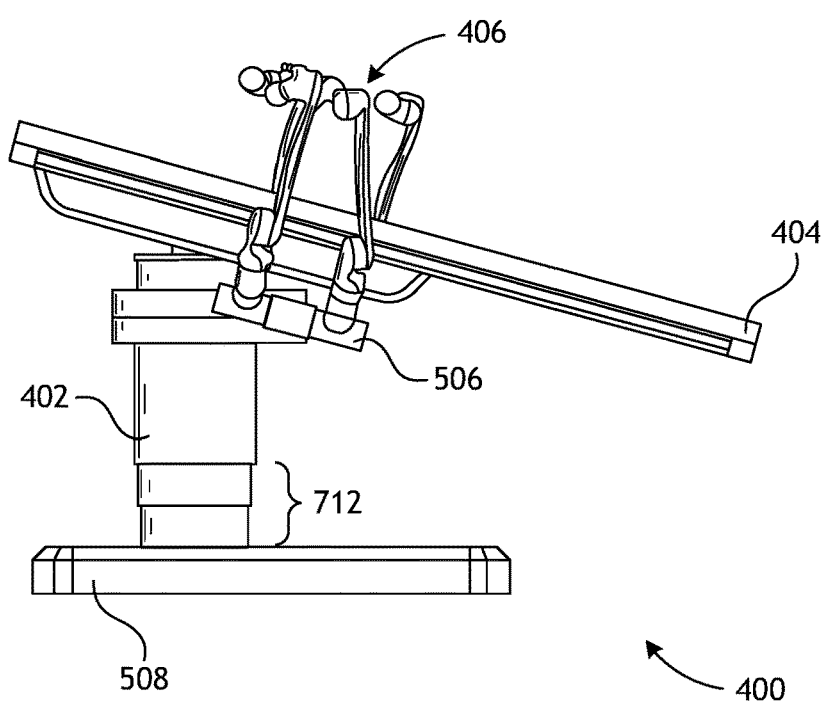
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
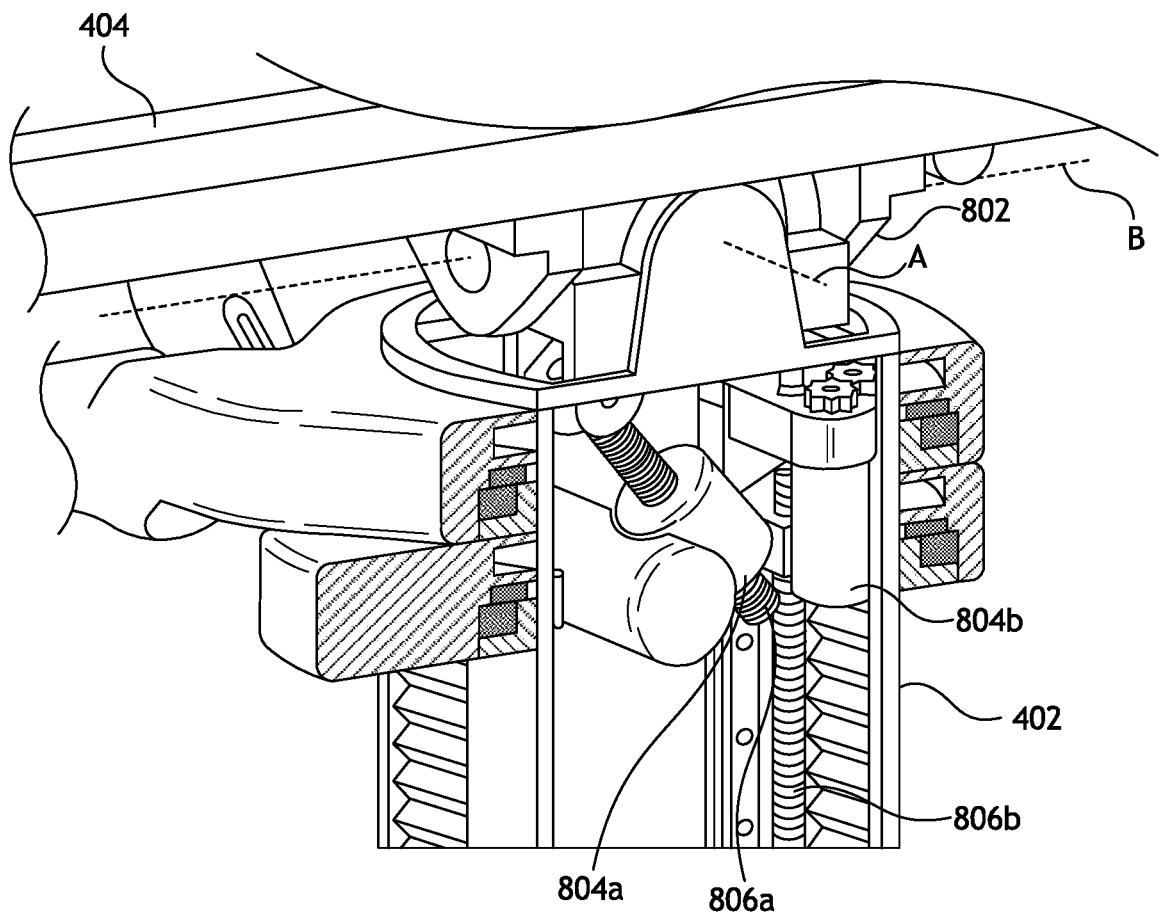
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
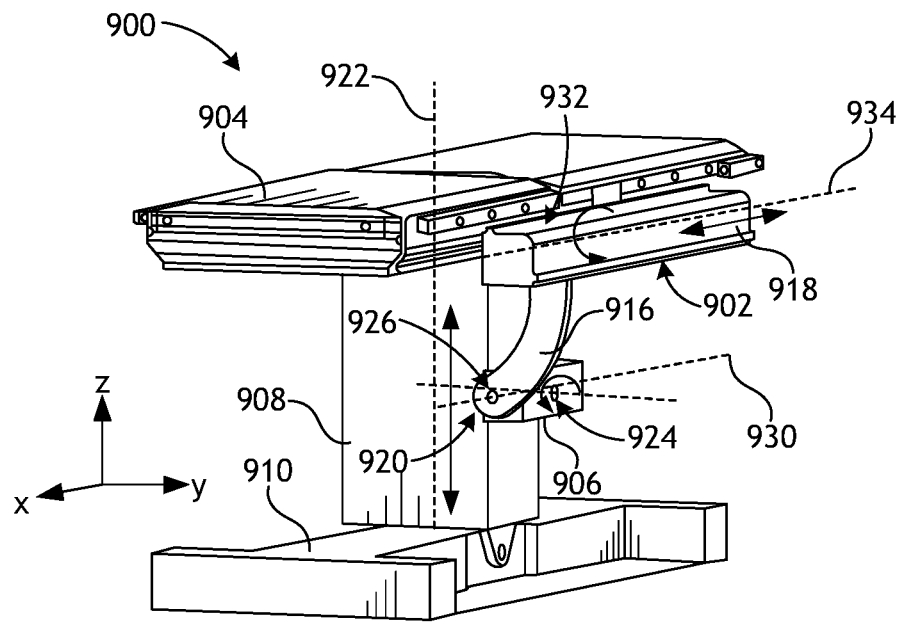
FIG. 9A illustrates an alternative embodiment of a table-based robotic system.
Figure 9B:
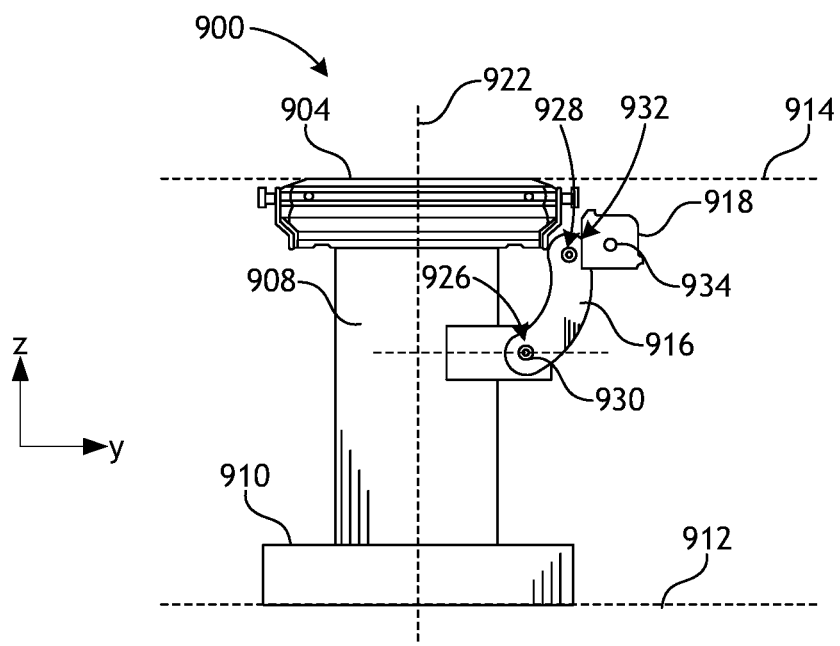
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
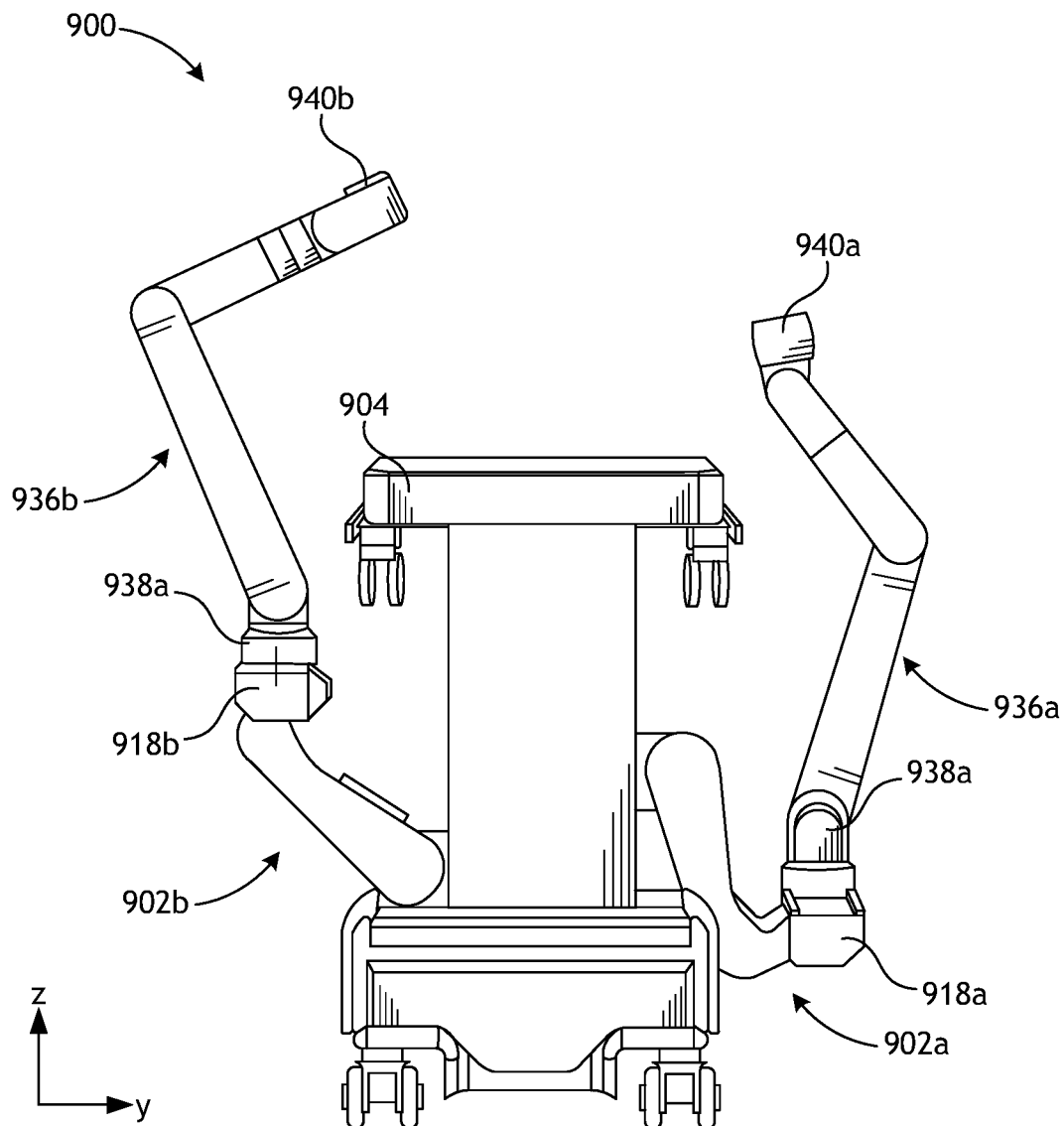
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electromechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
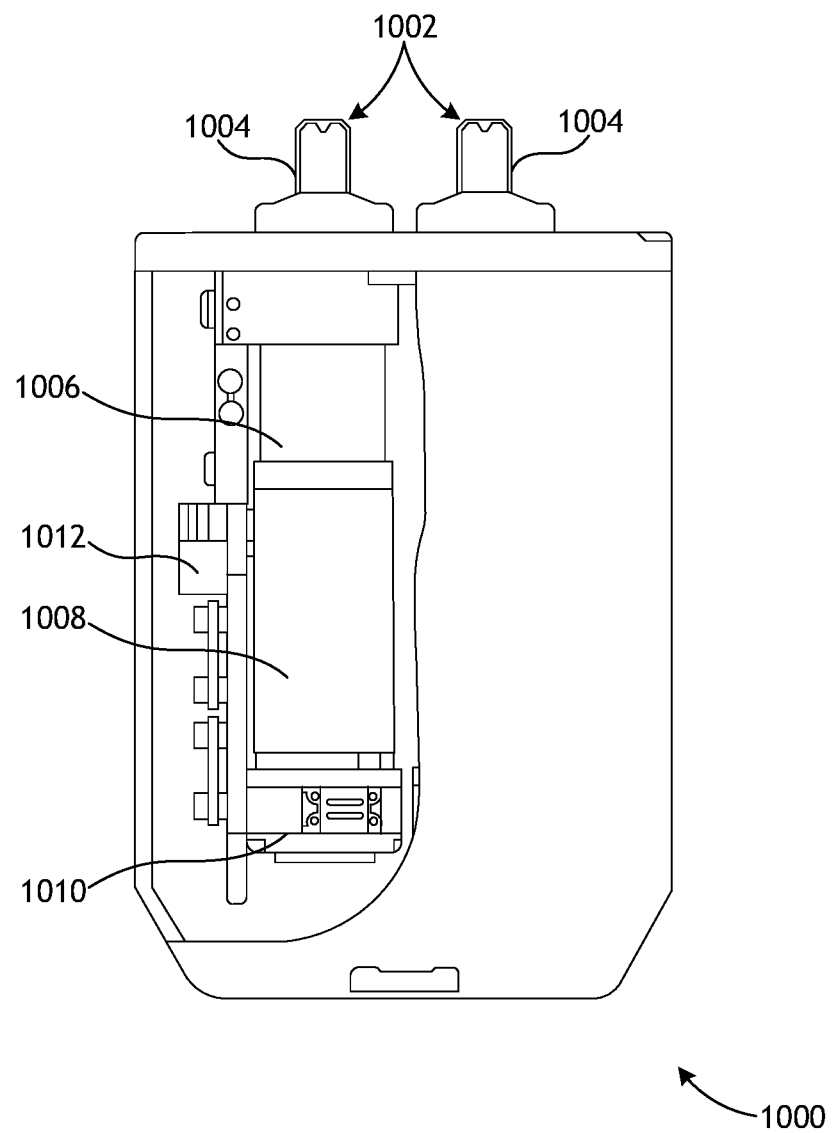
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
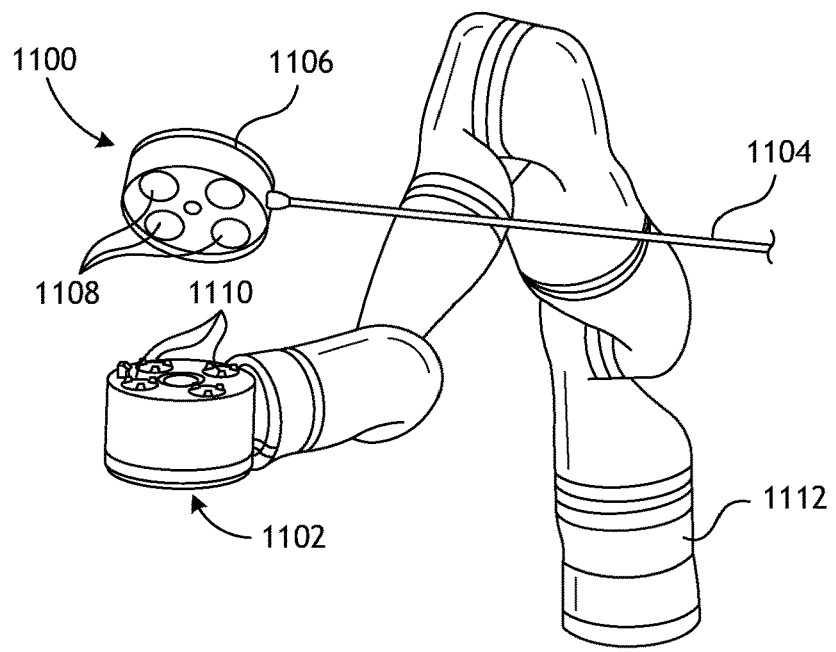
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
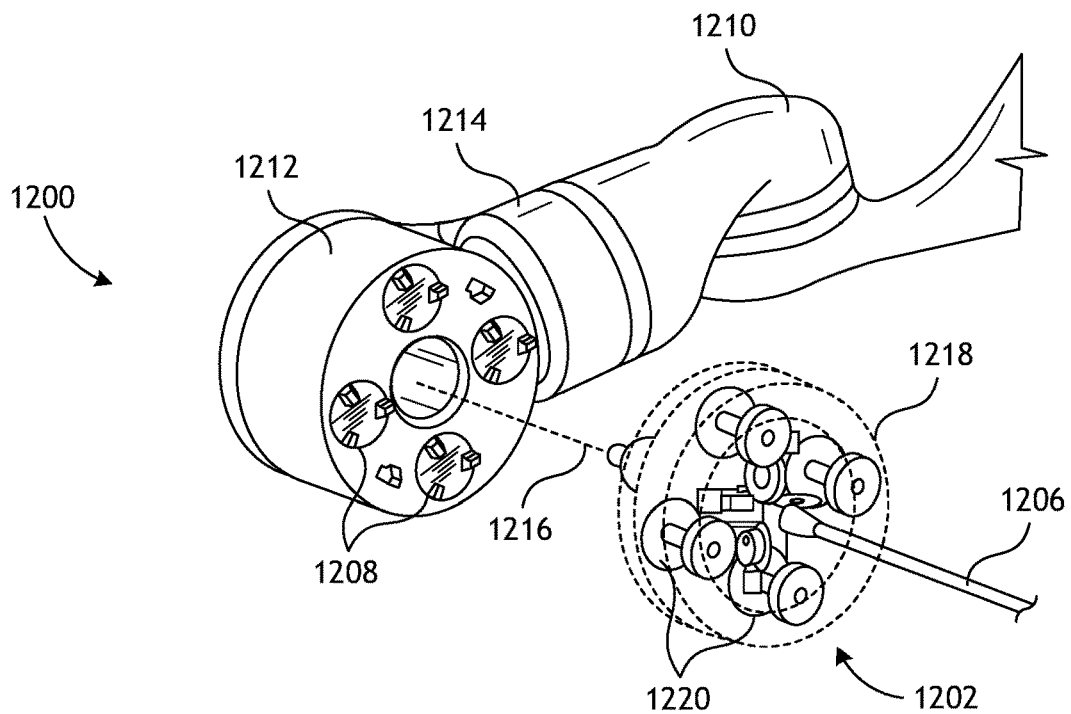
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
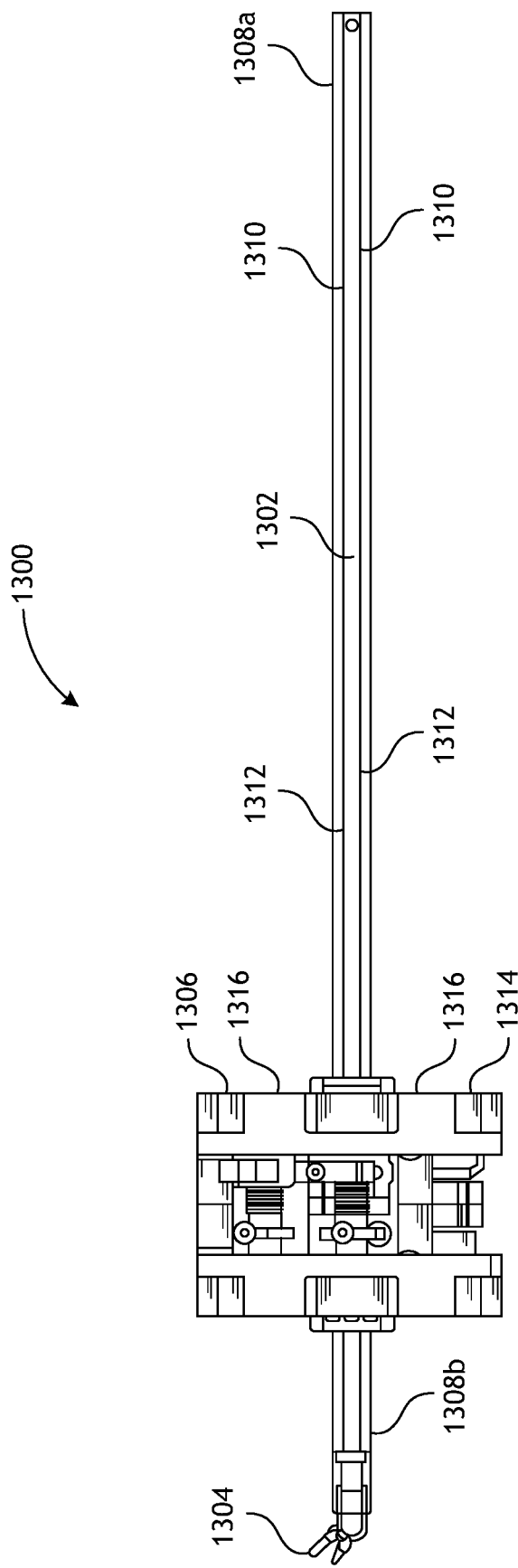
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308*a* and a distal portion 1308*b*. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
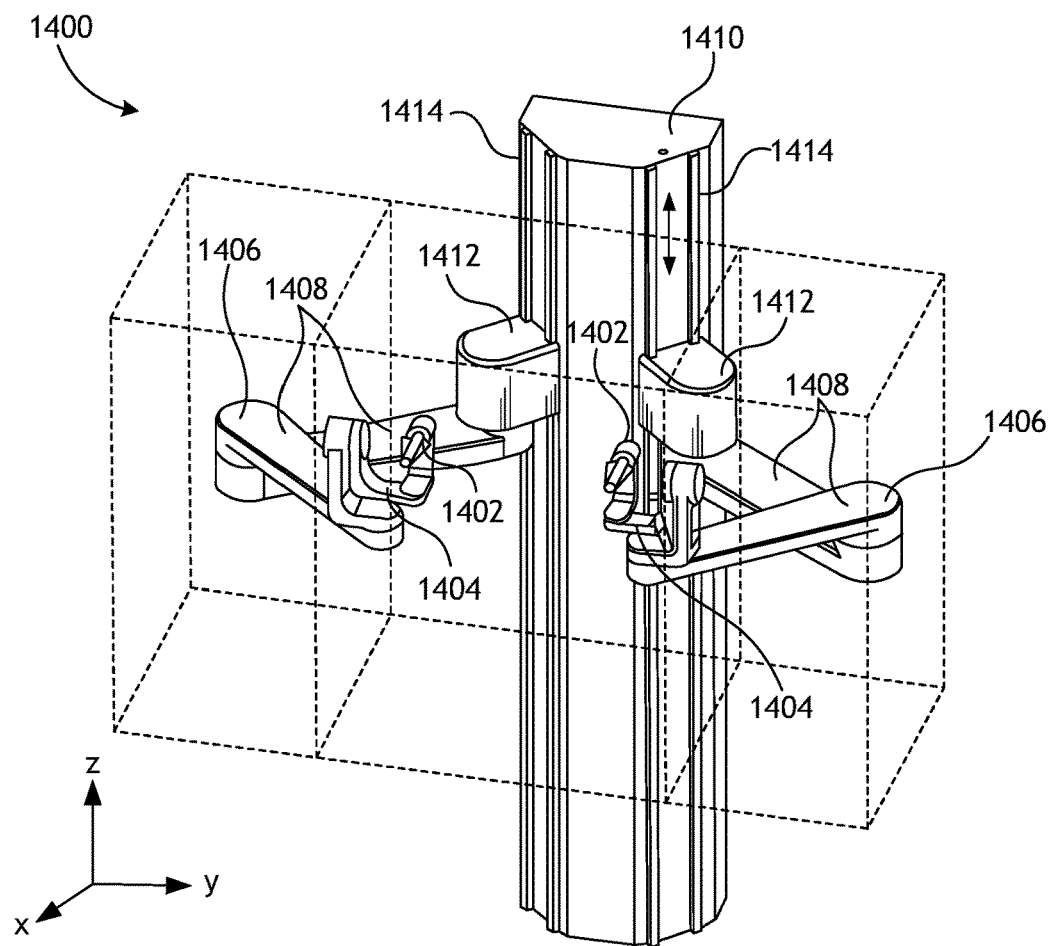
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
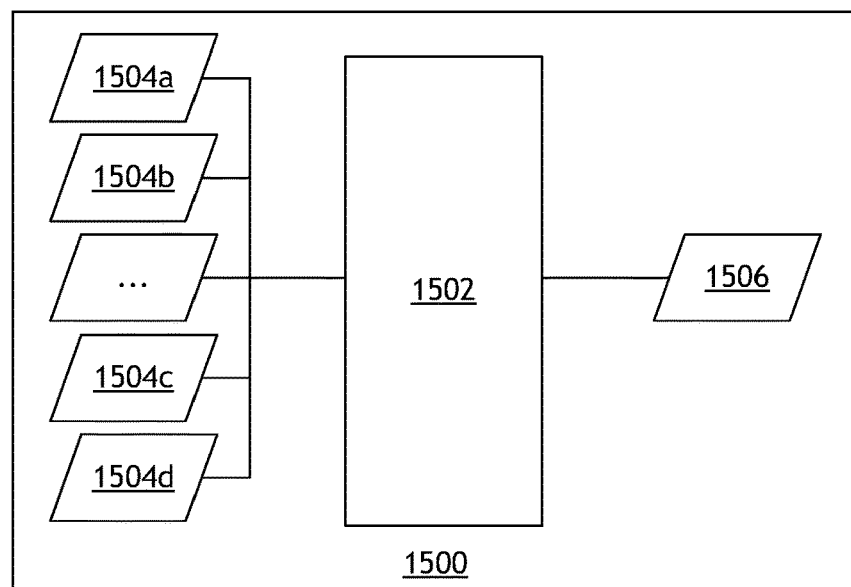
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Endoscope and Mounting System.

Embodiments of this disclosure relate to robotic surgical tools that include a handle and an elongate shaft extendable through the handle and including an outer proximal tube and an inner spline rotatably received within the outer proximal tube. A first actuation system housed within the handle may be operable to rotate the inner spline relative to the outer proximal tube and thereby transfer torque to a proximal or distal end of the shaft. A second actuation system housed within the handle may be operable to drive the outer proximal tube and thereby advance or retract the elongate shaft in z-axis translation through the handle.

Figure 16:
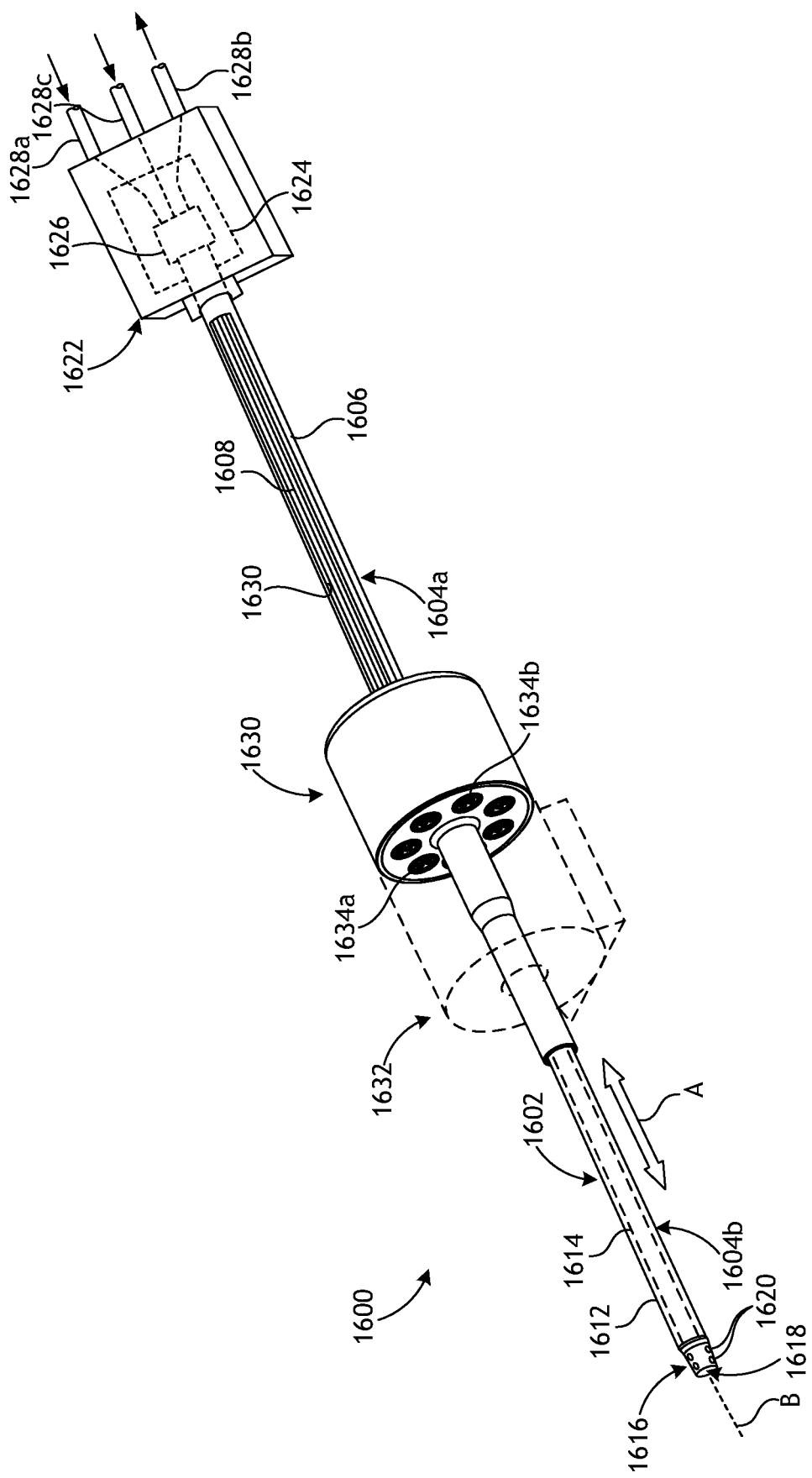
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. In the illustrated embodiment, the surgical tool 1600 comprises an irrigation/aspiration/blowing (IAB) robotic surgical tool, alternatively referred to as a "suction irrigator". The principles of the present disclosure, however, are equally applicable to other types of surgical tools, without departing from the scope of the disclosure.

As illustrated, the surgical tool 1600 includes an elongated shaft 1602 that can include a proximal shaft assembly 1604a and a distal shaft assembly 1604b operatively coupled to the proximal shaft assembly 1604a. The proximal shaft assembly 1604a includes an outer proximal tube 1606 and an inner spline 1608 rotatably received within the outer proximal tube 1606. In some embodiments, the inner spline 1608 may comprise a length of pinion wirestock defining outer gear teeth. As illustrated, a longitudinal slot 1610 may be defined along all or a portion of the outer proximal tube 1606. As discussed in more detail below, the slot 1610 may enable engagement with the gear teeth of the inner spline 1608 in order to drive the inner spline 1608 in rotation and thereby transfer torque to the proximal or distal end of the shaft 1602.

In at least one embodiment, the inner spline 1608 may be rifle drilled and otherwise define a lumen (not shown) configured to convey fluids (i.e., liquids, gases, vacuum, etc.) therethrough. In such embodiments, the inner spline 1608 may help support operation of the surgical tool 1600 as a suction irrigator. In other embodiments, however, the inner spline 1608 may comprise a solid shaft without departing from the scope of the disclosure.

The distal shaft assembly 1604b may include an outer distal tube 1612, an inner distal tube 1614 (shown in dashed lines) arranged within the outer distal tube 1612, and a distal tip 1616 arranged at a distal end of the shaft 1602 and fixed to the outer and inner distal tubes 1612, 1614. In some embodiments, the lumen defined within the inner spline 1608 may communicate with a corresponding lumen defined within the inner distal tube 1614. Consequently, the shaft 1602 may be characterized as a generally hollow tube capable of conveying fluids along its entire length in either direction. As used herein, the term "fluid" refers to any liquid or gas, but can also refer to a vacuum or any combination thereof. Moreover, the fluid may be conveyed within the shaft 1602 with or without the conveyance of solids.

The distal tip 1616 may define an opening 1618 configured to discharge or receive fluids. In some applications, for example, a fluid (e.g., water, a pressurized gas, etc.) may be conveyed through the shaft 1602 to the distal tip 1616 and discharged to a surgical site via the opening 1618 at the distal tip 1616. In other applications, however, a fluid (e.g., blood, water, etc.) may be drawn into the shaft 1602 at the distal tip 1616 from a surgical site and conveyed through the shaft 1602. In some embodiments, the distal tip 1616 may provide or define one or more smaller openings 1620 around its circumference to further allow fluids to flow into and out of a surgical site via the shaft 1602.

Figure 17A:
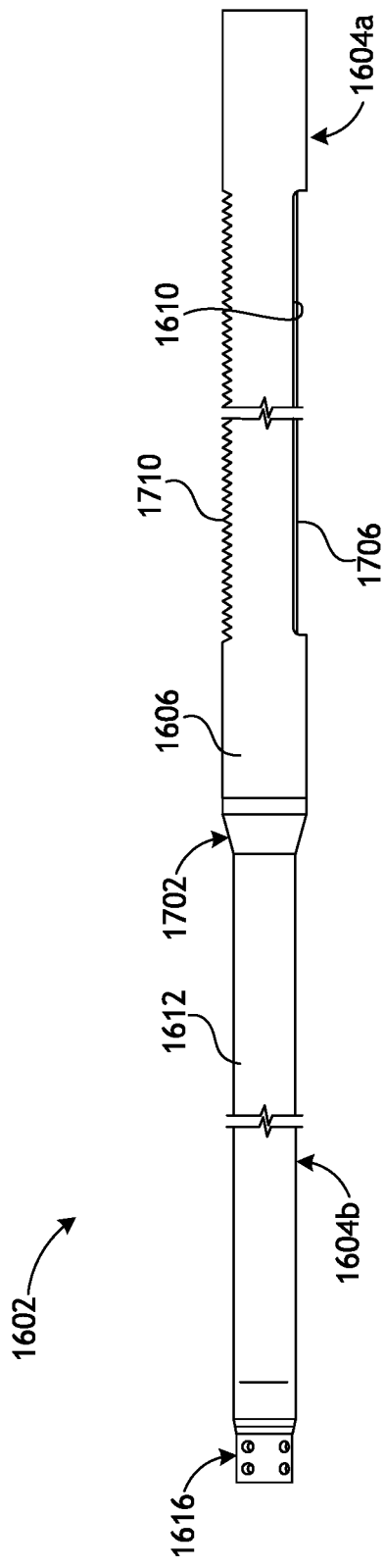
FIGS. 17A and 17B are side and cross-sectional side views, respectively, of the shaft of FIG. 16, according to one or more embodiments.
Figure 17B:
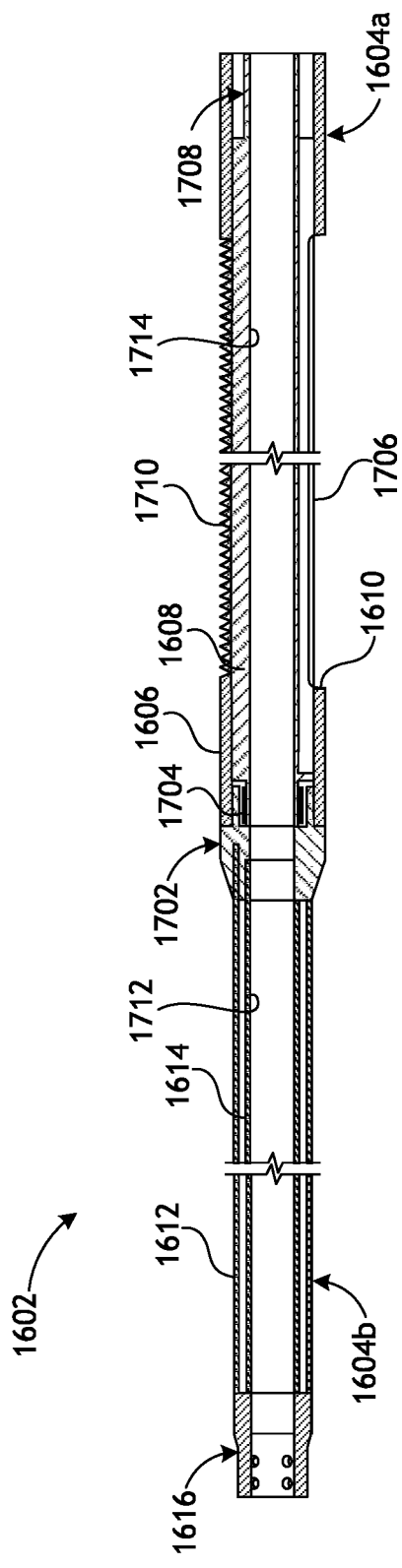

Referring briefly to FIGS. 17A and 17B, illustrated are side and cross-sectional side views, respectively, of the shaft 1602, according to one or more embodiments. As indicated above, the shaft 1602 includes the proximal and distal shaft assemblies 1604a,b, which may be coupled together at a connector 1702. The proximal shaft assembly 1604a extends proximally from the connector 1702, and the distal shaft assembly 1604b extends distally from the connector 1702. The proximal shaft assembly 1604a includes the outer proximal tube 1606 and the inner spline 1608 rotatably received within the outer proximal tube 1606. The outer proximal tube 1606 may be fixed to the connector 1702, but the inner spline 1608 may be rotatably coupled to the connector 1702. In one or more embodiments, for example, the distal end of the inner spline 1608 may be rotatably received within a corresponding portion of the connector 1702. In such embodiments, one or both of the distal end of the inner spline 1608 or the connector 1702 may be made of a lubricious material or otherwise polished to allow the inner spline 1608 to rotate relative to the connector 1702 with little or no resistance. In other embodiments, however, a low-friction bushing or bearing 1704 (FIG. 17B) may be arranged between the distal end of the inner spline 1608 and the connector 1702, without departing from the scope of the disclosure.

The longitudinal slot 1610 may be defined along a portion of the outer proximal tube 1606 to enable access to the inner spline 1608. More specifically, the slot 1610 exposes a series of longitudinally-extending gear teeth 1706 defined on the inner spline 1608, and the gear teeth 1706 may be engaged and driven by a corresponding drive gear (not shown) in order to rotate the inner spline 1608 within the outer proximal tube 1606. In one or more embodiments, the proximal end of the inner spline 1608 may provide or define an adapter 1708 (FIG. 17B) configured to mate with an adjacent mechanism or device (not shown) such that rotation of the inner spline 1608 transfers torque to the proximal end of the inner spline and thereby causes the mechanism or device to actuate. In at least one embodiment, for example, the adapter 1708 may mate with one or more valves (not shown) actuatable via rotation of the inner spline 1608 to cause a fluid to be conveyed through the shaft 1602 in either direction. In other embodiments, however, the adapter 1708 may mate with a variety of other mechanisms or devices configured to be actuated via rotation of the inner spline 1608.

In some embodiments, as illustrated, a rack 1710 may be defined or otherwise provided on the outer proximal tube 1606 and provide a series of gear teeth. As discussed in more detail below, the gear teeth of the rack 1710 may be configured to be engaged and driven by a corresponding pinion gear (not shown) in order to drive (move) the entire shaft 1602 in z-axis translation.

The distal shaft assembly 1604b includes the outer distal tube 1612 and the inner distal tube 1614 arranged within the outer distal tube 1612. The distal ends of the outer and inner distal tubes 1612, 1614 may each be fixed to the distal tip 1616, and the proximal ends of the outer and inner distal tubes 1612, 1614 may each be fixed to the connector 1704. As best seen in FIG. 17B, in some embodiments, the inner distal tube 1614 may define a first lumen 1712 and the inner spline 1608 may define a second lumen 1714 in fluid communication with the first lumen 1712 via the connector 1704. In such embodiments, fluids (i.e., liquids, gases, vacuum, etc.) are able to traverse the entire length of the shaft 1602 by passing through the interconnected lumens 1712, 1714, thus helping to support operation of the surgical tool 1600 (FIG. 16) as a suction irrigator. In some embodiments, the interconnection between the connector 1702 and the inner spline 1608 and the inner distal tube 1614 provides a sealed interface, while allowing rotation of the inner spline 1608 relative to the connector 1704.

Referring again to FIG. 16, the surgical tool 1600 may further include a tailpiece 1622 arranged at a proximal end of the shaft 1602 and otherwise coupled to the proximal end of the proximal shaft assembly 1604a. In some embodiments, the tailpiece 1622 may include a flow control system 1624 operable to control the flow of fluids (including any solids that may be transported by the fluids) between a surgical site and the shaft 1602, or vice versa. In the illustrated embodiment, the flow control system 1624 may include one or more valves 1626 (shown as a dashed box) operatively coupled to the proximal end of the shaft 1602 and, more specifically, to the adapter 1708 (FIG. 17B) provided at the proximal end of the inner spline 1608. The inner spline 1608 may be operatively coupled to the valve(s) 1626 at the adapter 1708 such that rotation of the inner spline 1608 correspondingly alters operation of the valve(s) 1626 to enable or prohibit the flow of fluids through the shaft 1602 in either direction.

In some embodiments, the tailpiece 1622 may have one or more hoses or conduits extending therefrom and in fluid communication with the flow control system 1624. In the illustrated embodiment, a first conduit 1628a, a second conduit 1628b, and a third conduit 1628c are included. The first conduit 1628a may be configured to convey a liquid (e.g., water) to the surgical tool 1600 to be discharged from the shaft 1602 at the distal tip 1616 for irrigation purposes. The second conduit 1628b may draw a vacuum and may otherwise be configured draw fluids (e.g., blood, water, air, etc.) through the shaft 1602 from the surgical site. Lastly, the third conduit 1628c may be configured to convey a compressed gas (e.g., air) to the surgical tool 1600 to be discharged from the shaft 1602 at the distal tip 1616 for blowing. Rotation of the inner spline 1608 causes the valve(s) 1626 to switch operation between the conduits 1628a-c or any combination thereof.

Still referring to FIG. 16, the surgical tool 1600 may include a drive housing or "handle" 1630, and the shaft 1602 extends longitudinally through the handle 1630. The handle 1630 houses various actuation systems designed to operate the surgical tool 1600. At least one actuation system, for example, may be designed to move the shaft 1602 relative to the handle 1630 in z-axis translation, as indicated by the arrows A, and thereby advance or retract the distal tip 1616. Another actuation system may be designed to drive the inner spline 1608 in rotation, and thereby actuate the valve(s) 1626 to control fluid flow through the shaft 1602. In other embodiments, however, driving the inner spline 1608 in rotation may alternatively actuate other devices or mechanisms, without departing from the scope of the disclosure.

The handle 1630 provides or otherwise includes various coupling features (not shown) that releasably couple the surgical tool 1600 to an instrument driver 1632 (shown in dashed lines) of a robotic surgical system. The instrument driver 1632 may be similar in some respects to the instrument drivers 1102, 1200 of FIGS. 11 and 12, respectively, and therefore may be best understood with reference thereto. Similar to the instrument drivers 1102, 1200, for example, the instrument driver 1632 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1632.

The handle 1630 includes one or more rotatable drive inputs matable with one or more corresponding drive outputs (not shown) of the instrument driver 1632. Each drive input is actuatable to independently drive (actuate) the actuation systems and mechanisms housed within the handle 1630 and thereby operate the surgical tool 1600. In the illustrated embodiment, the handle 1630 includes at least a first drive input 1634a and a second drive input 1634b. The drive inputs 1634a,b may be matable with corresponding drive outputs (not shown) of the instrument driver 1632 such that movement (rotation) of a given drive output correspondingly moves (rotates) the associated drive input 1634a,b and thereby causes various operations of the surgical tool 1600. In some embodiments, actuation of the first drive input 1634a may cause the shaft 1602 to move (translate) relative to the handle 1630 along a longitudinal axis B, depending on the rotational direction of the first drive input 1634a. Moreover, actuation of the second drive input 1634b may drive the inner spline 1608 in rotation, which may cause the valve(s) 1626 to actuate and control fluid flow through the shaft 1602.

Figure 18:
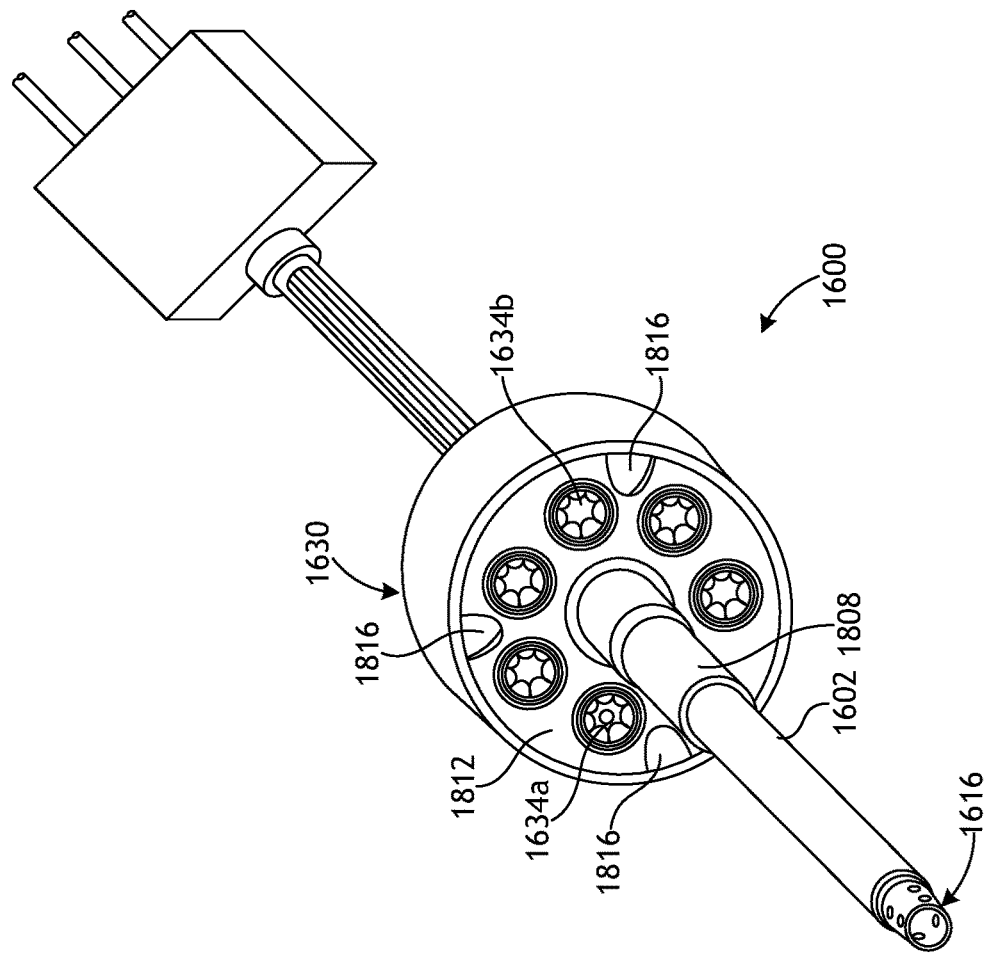
FIG. 18 depicts separated isometric end views of the instrument driver and the surgical tool of FIG. 16.
Figure 18:
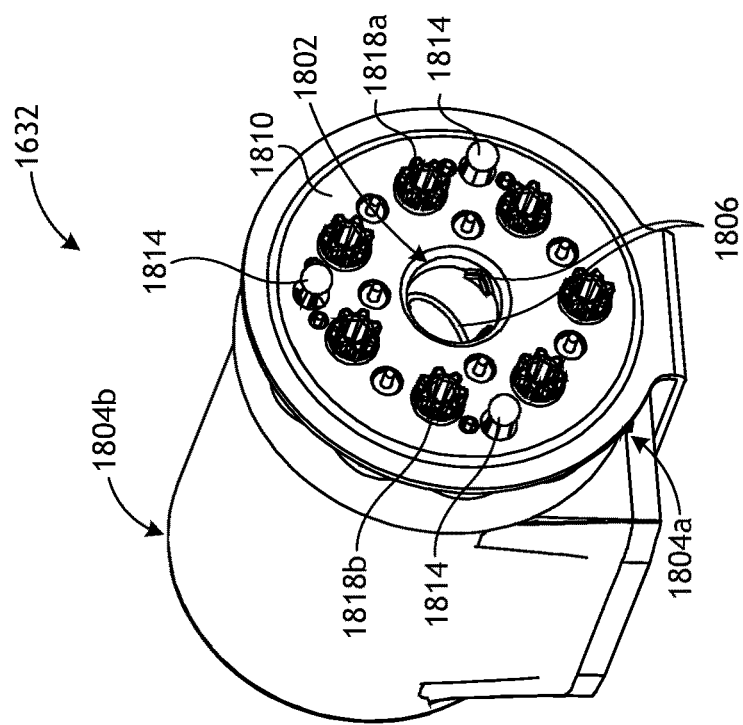

FIG. 18 depicts separated isometric end views of the instrument driver 1632 and the surgical tool 1600 of FIG. 16. The shaft 1602 and the distal tip 1616 can penetrate the instrument driver 1632 by extending through a central aperture 1802 defined longitudinally through the instrument driver 1632 between first and second ends 1804a,b. In some embodiments, to align the surgical tool 1600 with the instrument driver 1632 in a proper angular orientation, one or more alignment guides 1806 may be provided or otherwise defined within the central aperture 1802 and configured to engage one or more corresponding alignment features (not shown) provided on the surgical tool 1600. The alignment feature(s) may comprise, for example, a protrusion or projection (not shown) defined on or otherwise provided by an alignment nozzle 1808 extending distally from the handle 1630. In one or more embodiments, the alignment guide(s) 1806 may comprise a curved or arcuate shoulder or lip configured to receive and guide the alignment feature as the alignment nozzle 1808 enters the central aperture 1802. As a result, the surgical tool 1600 is oriented to a proper angular alignment with the instrument driver 1632 as the alignment nozzle 1808 is advanced distally through the central aperture 1802. In other embodiments, the alignment nozzle 1808 may be omitted and the alignment feature may alternatively be provided on the shaft 1602, without departing from the scope of the disclosure.

A drive interface 1810 is provided at the first end 1804a of the instrument driver 1632 and is matable with a driven interface 1812 provided on the distal end of the handle 1630. The drive and driven interfaces 1810, 1812 may be configured to mechanically, magnetically, and/or electrically couple the handle 1630 to the instrument driver 1632. To accomplish this, in some embodiments, the drive and driven interfaces 1810, 1812 may provide one or more matable locating features configured to secure the handle 1630 to the instrument driver 1632. In the illustrated embodiment, for example, the drive interface 1810 provides one or more interlocking features 1814 (three shown) configured to locate and mate with one or more complementary-shaped pockets 1816 (two shown, one occluded) provided on the driven interface 1812. In some embodiments, the features 1814 may be configured to align and mate with the pockets 1816 via an interference or snap fit engagement, for example.

The instrument driver 1632 also includes one or more drive outputs that extend through the drive interface 1810 to mate with corresponding drive inputs provided at the distal end of the handle 1630. More specifically, the instrument driver 1632 includes at least a first drive output 1818a matable with the first drive input 1634a, and a second drive output 1818b matable with the second drive input 1634b. In some embodiments, as illustrated, the drive outputs 1818a,b may define splines or features designed to mate with corresponding splined receptacles of the drive inputs 1634a,b. Once properly mated, the drive inputs 1634a,b will share axes of rotation with the corresponding drive outputs 1818a,b to allow the transfer of rotational torque from the drive outputs 1818a,b to the corresponding drive inputs 1634a,b. In some embodiments, each drive output 1818a,b may be spring loaded and otherwise biased to spring outwards away from the drive interface 1810, and each drive output 1818a,b may be capable of partially or fully retracting into the drive interface 1810.

While not shown, in some embodiments, an instrument sterile adapter (ISA) may be placed at the interface between the instrument driver 1632 and the handle 1630. In such applications, the interlocking features 1814 may operate as alignment features and possible latches for the ISA to be placed, stabilized, and secured. Stability of the ISA may be accomplished by a nose cone feature provided by the ISA and extending into the central aperture 1802 of the instrument driver 1632. Latching can occur either with the interlocking features 1814 or at other locations at the interface. In some cases, the ISA will provide the means to help align and facilitate the latching of the surgical tool 1600 to the ISA and simultaneously to the instrument driver 1632.

Figure 19:
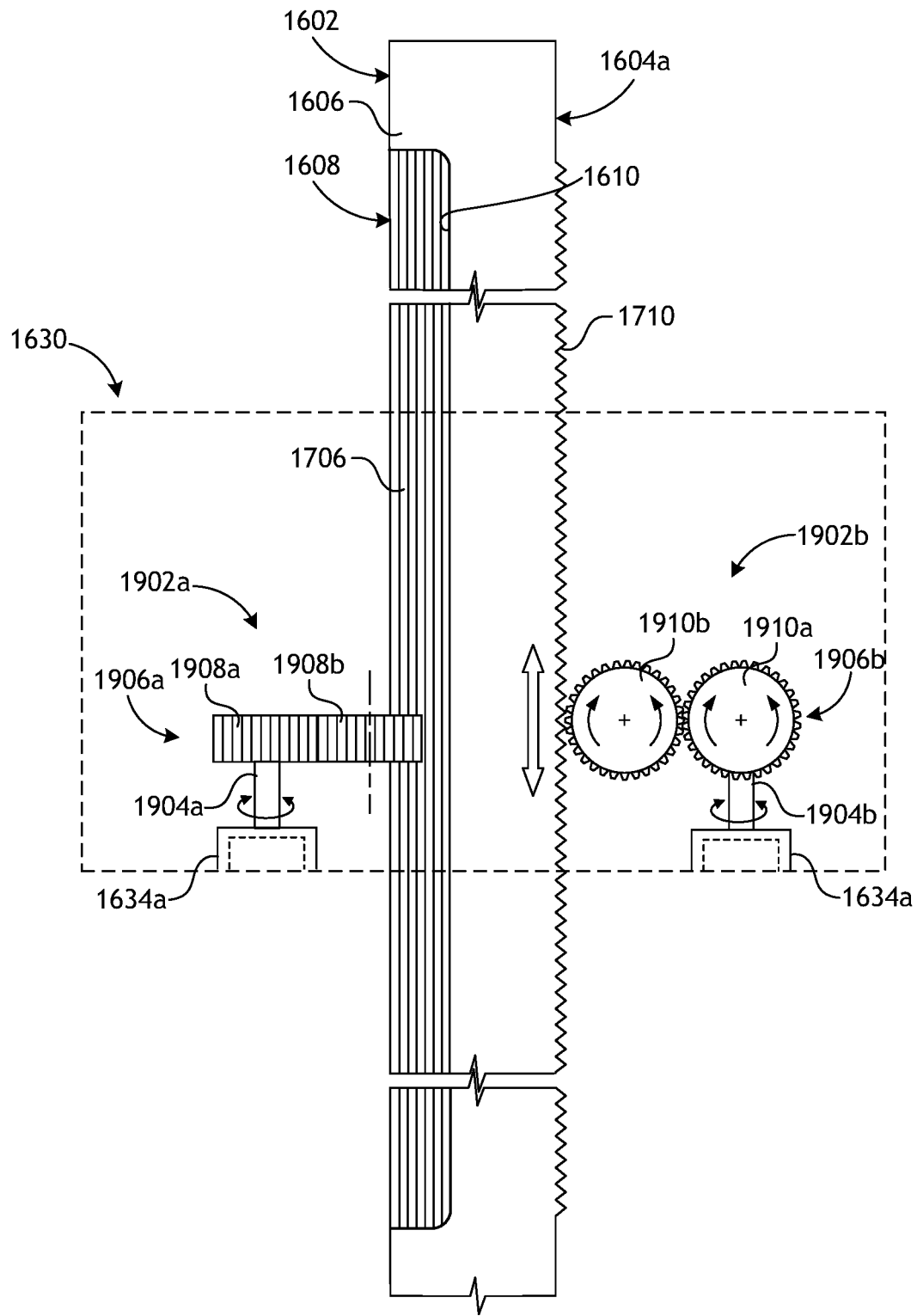
FIG. 19 is an enlarged schematic side view of one example of the handle of FIGS. 16 and 18, according to one or more embodiments of the present disclosure.

FIG. 19 is an enlarged schematic side view of one example of the handle 1630 of FIGS. 16 and 18, according to one or more embodiments of the present disclosure. The outer body of the handle 1630 is shown in phantom (dashed lines) to enable viewing of the internal space and component parts within the handle 1630. It should be noted that various actuation systems and component parts of the handle 1630 are omitted in FIG. 19 for simplicity.

As illustrated, the shaft 1602 is able to extend through the handle 1630. More particularly, the proximal shaft assembly 1604a, including the outer proximal tube 1606 and the inner spline 1608, may extend longitudinally through the handle 1630. The longitudinal slot 1610 defined along the outer proximal tube 1606 exposes the inner spline 1608 and thereby allows the inner spline 1608 to be driven in rotation relative to the outer proximal tube 1606. As mentioned above, rotation of the inner spline 1608 may actuate the valve(s) 1626 (FIG. 16) included in the tailpiece 1622 (FIG. 16), but could alternatively actuate or operate a variety of other mechanisms or devices. Moreover, the rack 1710 is depicted on the outer proximal tube 1606 and thereby provides a series of gear teeth configured to be engaged and driven to cause the shaft 1602 to move in z-axis translation relative to the handle 1630.

As illustrated, the handle 1630 may include a first actuation system 1902a and a second actuation system 1902b. The actuation systems 1902a,b may be operable (actuatable) to carry out a variety of functions (operations) of the surgical tool 1600 (FIG. 16). In the illustrated embodiment, however, the first actuation system 1902a may be designed and otherwise configured to drive the inner spline 1608 in rotation, and thereby actuate the valve(s) 1626 (FIG. 16). Moreover, the second actuation system 1902b may be operable to cause the shaft 1602 to move relative to the handle 1630 and thereby longitudinally advance or retract the distal tip 1616 (FIGS. 16 and 18) in z-axis translation.

In the illustrated embodiment, the first actuation system 1902a includes a first drive shaft 1904a coupled to or forming part of the first drive input 1634a such that rotation of the first drive input 1634a correspondingly rotates the first drive shaft 1904a in the same direction. Rotating the first drive input 1634a may operate or actuate a first drive mechanism 1906a that may include any of a variety of interconnected gears, belts, chains, sprockets, etc. configured to ultimately drive the inner spline 1608 in rotation. In the illustrated embodiment, the first drive mechanism 1906a comprises a gear train that includes an input gear 1908a and a drive gear 1908b. More specifically, the input gear 1908a may be driven by rotation of the first drive shaft 1904a and may be arranged to drive the drive gear 1908b, and the drive gear 1908b may intermesh with the longitudinally-extending gear teeth 1706 defined on the inner spline 1608. Accordingly, rotation (actuation) of the first drive shaft 1904a may correspondingly drive (rotate) the inner spline 1608 and thereby actuate the valve(s) 1626 (FIG. 16).

While the first drive mechanism 1906a depicted in FIG. 19 includes two geared components to drive the inner spline 1608, those skilled in the art will readily appreciate that the first drive mechanism 1906a may alternatively include more or less than two geared components. Indeed, the depicted first drive mechanism 1906a is but one example of a geared system or arrangement designed to drive the inner spline 1608, and various other designs or configurations of the first drive mechanism 1906a may alternatively be incorporated into the first actuation system 1902a to drive (rotate) the inner spline 1608, without departing from the scope of the disclosure.

The second actuation system 1902b includes a second drive shaft 1904b coupled to or forming part of the second drive input 1634b such that rotation of the second drive input 1634b correspondingly rotates the second drive shaft 1904b in the same direction. Rotating the second drive input 1634a may operate or actuate a second drive mechanism 1906b that ultimately engages and drives the rack 1710 provided on the outer proximal tube 1606. Similar to the first drive mechanism 1906a, the second drive mechanism 1906b may include any of a variety of interconnected gears, belts, chains, sprockets, etc. In the illustrated embodiment, however, the second drive mechanism 1906b comprises a gear train that includes at least an input gear 1910a and a pinion gear 1910b. More specifically, the input gear 1910a may be driven by rotation of the second drive shaft 1904b and may be arranged to drive the pinion gear 1910b, and the pinion gear 1910b may intermesh with the rack 1710 provided on the outer proximal tube 1606. Accordingly, operating the second actuation system 1902b may cause the shaft 1602 to move relative to the handle 1630 and thereby longitudinally advance or retract the distal tip 1616 (FIGS. 16 and 18) in z-axis translation. Additionally, the drive gear 1908b of the first drive mechanism 1906a may be capable of sliding along the longitudinally-extending gear teeth 1706 defined on the inner spline 1608, thus allowing both actuation systems 1902a,b to operate simultaneously.

While the second drive mechanism 1906b depicted in FIG. 19 includes two geared components to drive the outer proximal tube 1606, those skilled in the art will readily appreciate that the second drive mechanism 1906b may alternatively include more or less than two geared components. Indeed, the depicted second drive mechanism 1906b is but one example of a geared system or arrangement designed to drive the outer proximal tube 1606, and various other designs or configurations of the second drive mechanism 1906b may alternatively be incorporated into the second actuation system 1902b, without departing from the scope of the disclosure.

Figure 20A:
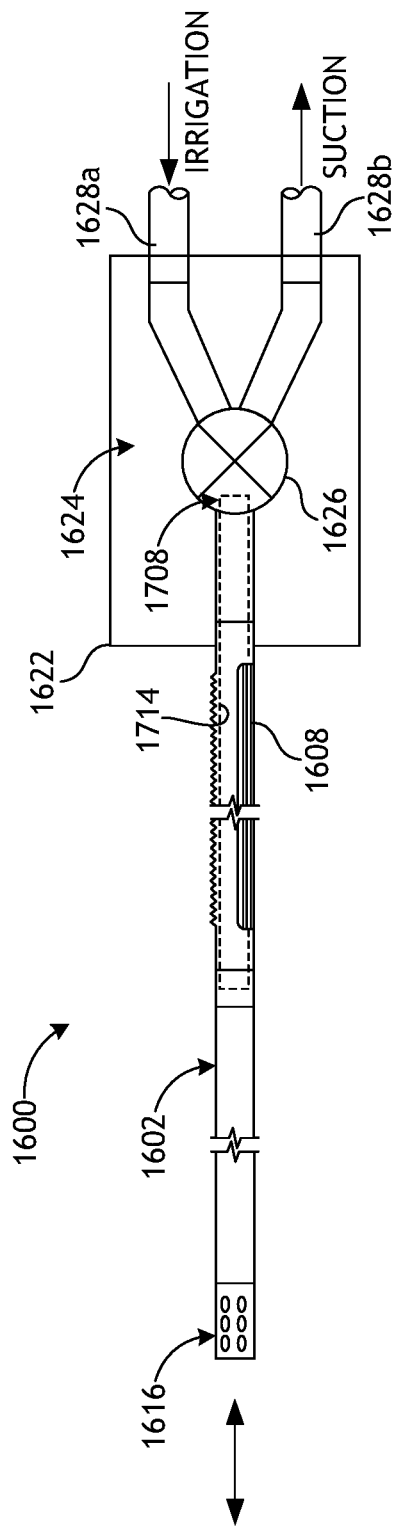
FIGS. 20A and 20B are schematic side views of examples of the surgical tool of FIG. 16, according various embodiments of the present disclosure.
Figure 20B:
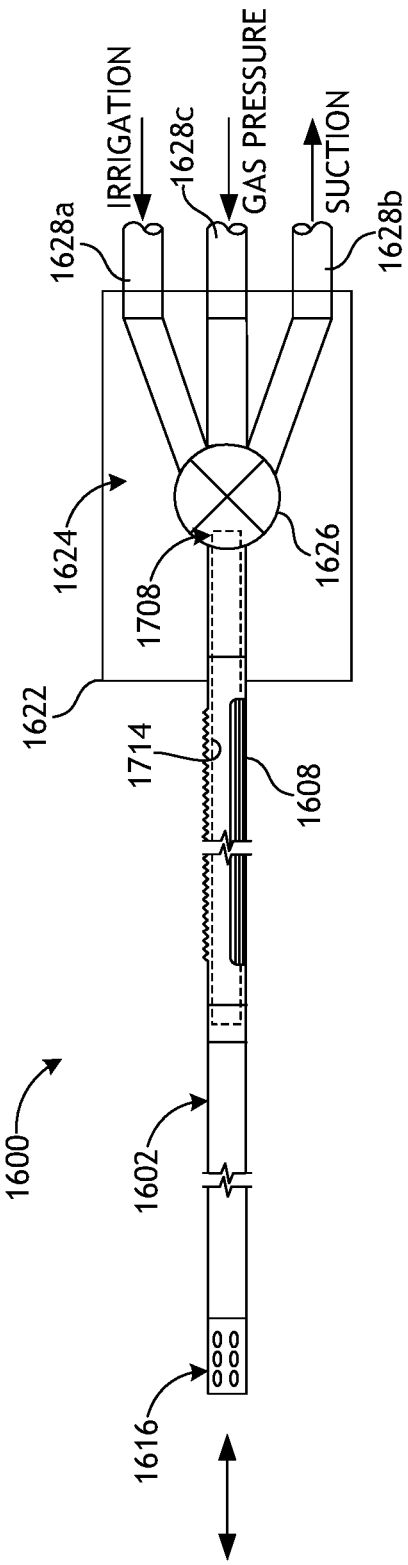

FIGS. 20A and 20B are schematic side views of examples of the surgical tool 1600, according various embodiments of the present disclosure. More specifically, FIGS. 20A-20B illustrate the shaft 1602 with the distal tip 1616 arranged at its distal end, and the tailpiece 1622 arranged at its proximal end. As briefly mentioned above, the flow control system 1624 provided within the tailpiece 1622 may include the valve 1626, which may comprise a rotary valve providing one or more of a vertical, axial, or horizontal stopcock. The valve 1626 may be actuatable (operable) to control the flow of fluids between a surgical site and the shaft 1602, or vice versa. More specifically, the adapter 1708 of the inner spline 1608 may be configured to mate with the valve 1626 such that rotation of the inner spline 1608 causes the valve 1626 to actuate and thereby alter the type and/or amount of fluid conveyed through the shaft 1602. Accordingly, actuation of the valve 1626 may provide irrigation, suction, blowing, or any combination thereof within a surgical site. Moreover, the shaft 1602 may be moved distally or proximally as the valve operates, as generally described above.

In FIG. 20A, the flow control system 1624 is configured to provide irrigation or aspiration capabilities. More specifically, the flow control system 1624 includes the first and second conduits 1628a,b, where the first conduit 1628a is configured to convey a liquid (e.g., water) through the shaft 1602 to be discharged at the distal tip 1616 for irrigation purposes, and the second conduit 1628b is configured to draw fluids (e.g., blood, water, air, etc.) through the shaft 1602 from the surgical site in suction. The flow control system 1624 in FIG. 20A incorporates a single valve 1626, which may comprise a three-way valve with three ports connecting the lumen 1714 defined within the inner spline 1608, the first conduit 1628a, and the second conduit 1628b.

In the illustrated embodiment, the valve 1626 has three positions of operation, and rotation of the inner spline 1608 may selectively place the valve 1626 in any of these positions. In a first or closed position, the valve 1626 is completely shut off so that no fluid flows through the shaft 1602 in either direction. In a second position, flow through the first conduit 1628a is allowed while flow through the second conduit 1628b is prevented thereby allowing the surgical site to be irrigated by a liquid flowing through the valve 1626 and into the shaft 1602. In a third position, flow through the second conduit 1628b is allowed while flow through the first conduit 1628a is prevented thereby creating a vacuum or a suction through the valve 1626 that aspirates the surgical site at the distal tip 1616.

In FIG. 20B, the flow control system 1624 is configured to provide irrigation, aspiration, or blowing, depending on the operable position of the valve 1626. In the illustrated embodiment, the flow control system 1624 includes the first, second, and third conduits 1628a-c, where the first conduit 1628a is configured to convey a liquid (e.g., water) through the shaft 1602 to be discharged at the distal tip 1616 for irrigation purposes, the second conduit 1628b is configured to draw fluids (e.g., blood, water, air, etc.) through the shaft 1602 from the surgical site, and the third conduit 1628c provides a pressurized gas for blowing at the surgical site. The flow control system 1624 again incorporates a single valve 1626, but the valve 1626 in this embodiment may comprise a four-way valve with four ports connecting the lumen 1714 and the conduits 1628a-c.

In the illustrated embodiment, the valve 1626 has four positions of operation, and rotation of the inner spline 1608 may selectively place the valve 1626 in any of these positions. In a first or closed position, the valve 1626 is completely shut off so that no fluid flows through the shaft 1602 in either direction. In a second position, flow through the first conduit 1628a is allowed while flow through the second and third conduits 1628b is prevented thereby allowing the surgical site to be irrigated by a liquid flowing through the valve 1626 and into the shaft 1602. In a third position, flow through the second conduit 1628b is allowed while flow through the first and third conduits 1628a is prevented thereby creating a vacuum or a suction through the valve 1626 that aspirates the surgical site at the distal tip 1616. In a fourth position, flow through the third conduit 1628c is allowed while flow through the first and second conduits 1628a,b is prevented, thereby allowing a pressurized gas (e.g., air) to flow through valve 1626 and out the distal tip 1616 of the shaft 1602 to blow a surgical site with pressurized gas.

Figure 21:
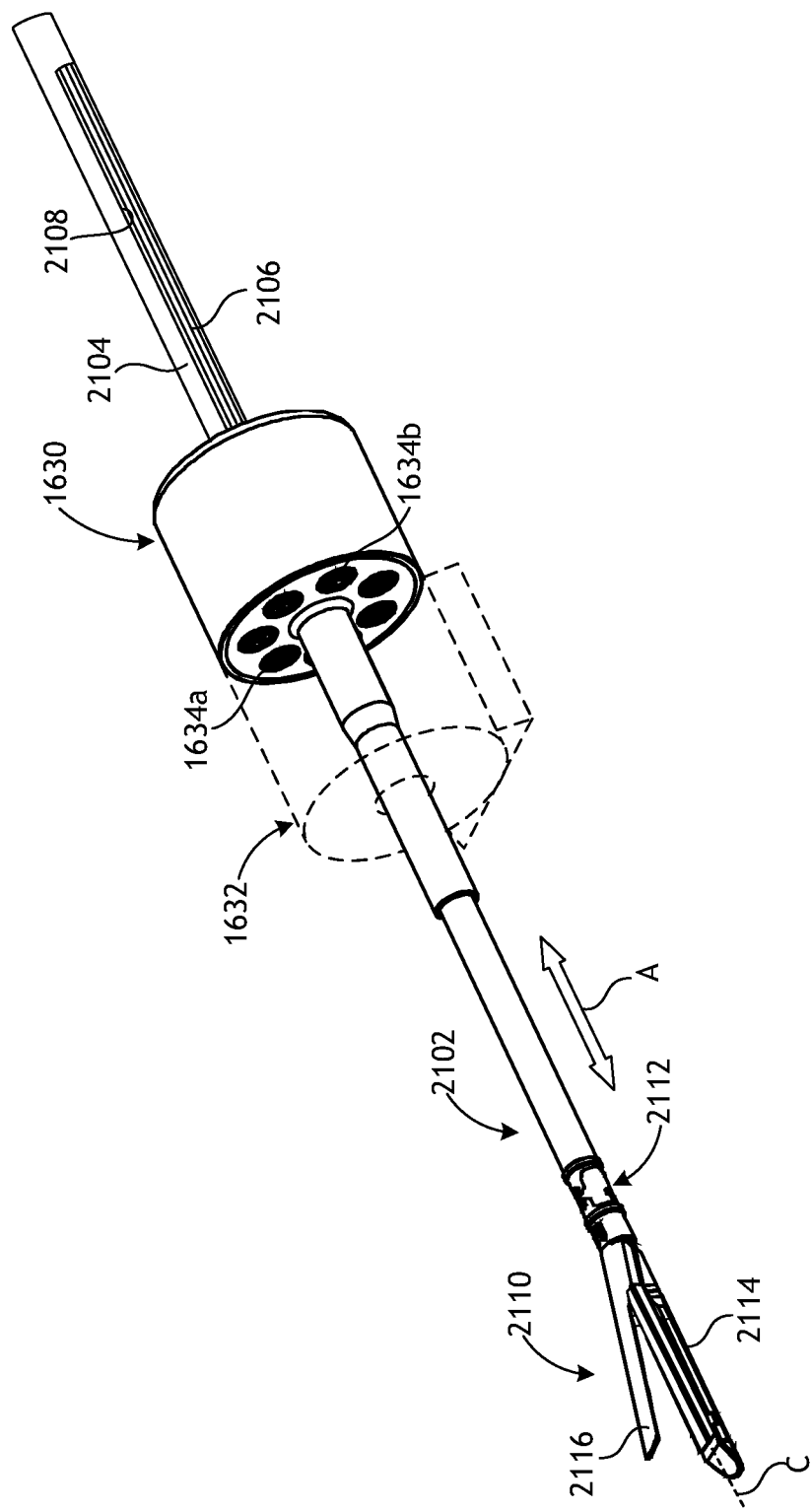
FIG. 21 is an isometric side view of another example surgical tool that may incorporate some or all of the principles of the present disclosure.

FIG. 21 is an isometric side view of another example surgical tool 2100 that may incorporate some or all of the principles of the present disclosure. The surgical tool 2100 may be similar in some respects to the surgical tool 1600 of FIGS. 16 and 18, and therefore may be best understood with reference thereto, where like numerals will correspond to like components not described again in detail. Similar to the surgical tool 1600, for example, the surgical tool 2100 may include an elongated shaft 2102 extendable through the handle 1630. The shaft 2102 may include an outer tube 2104 and an inner spline 2106 rotatably received within the outer tube 2104. The inner spline 2106 may be similar to the inner spline 1608 of FIGS. 16 and 17A-17B and, therefore, may comprise a length of pinion wirestock defining longitudinally-extending gear teeth. Moreover, the outer tube 2104 may define a longitudinal slot 2108 that enables engagement with the gear teeth of the inner spline 2106 in order to drive the inner spline 2106 in rotation.

The handle 1630 may be releasably coupled to the instrument driver 1632 (shown in dashed lines) and may house various actuation systems that operate the surgical tool 2100. One actuation system, for example, may include the first drive input 1634a and, therefore, may be designed to move the shaft 2102 relative to the handle 1630 in z-axis translation, as indicated by the arrows A. Another actuation system may include the second drive input 1634b and, therefore, may be designed to drive the inner spline 2106 in rotation. As described below, rotating the inner spline 2106 may actuate various devices or mechanisms included in the surgical tool 2100.

Unlike the surgical tool 1600 of FIGS. 16 and 18, however, the surgical tool 2100 may further include an end effector 2110 arranged at the distal end of the shaft 2102 and an articulable wrist 2112 (alternately referred to as a "wrist joint") that interposes and couples the end effector 2110 to the distal end of the shaft 2102. In the illustrated embodiment, the end effector 2110 comprises a surgical stapler configured to simultaneously cut and staple (fasten) tissue. As illustrated, the end effector 2110 includes opposing jaws 2114, 2116 configured to move (articulate) between open and closed positions. Alternatively, the end effector 2110 may comprise other types of instruments with opposing jaws such as, but not limited to, other types of surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc.

The wrist 2112 enables the end effector 2110 to articulate (pivot) relative to the shaft 2102 and thereby position the end effector 2110 at various desired orientations and locations relative to a surgical site. In the illustrated embodiment, the wrist 2112 is designed to allow the end effector 2110 to pivot (swivel) left and right relative to a longitudinal axis C of the shaft 2102, but could alternatively be designed to provide multiple degrees of freedom.

Moreover, unlike the surgical tool 1600, rotating the inner spline 2106 of the surgical tool 2100 will not facilitate operation of a suction irrigator, but may instead facilitate articulation of the wrist 2112 and/or actuation (operation) of the end effector 2110 (e.g., clamping, firing, rotation, articulation, energy delivery, etc.). In some embodiments, for example, the inner spline 2106 may extend within the outer tube 2104 to the end effector 2110 or adjacent thereto and may, therefore, transfer rotational torque from the handle 1630 to the end effector 2110 to open/close the jaws 2114, 2116, to articulate the wrist 2112, to cause distal roll of the end effector 2110, to "fire" the end effector 2110, any combination thereof, or other operations. In such embodiments, the inner spline 2106 may comprise a solid or tubular shaft. In other embodiments, however, the inner spline 2106 may define a lumen (e.g., the lumen 1714 of FIG. 17B), and a monopolar wire or the like could be run to the end effector 2110 to provide electrocautery capabilities to the end effector 2110. In such embodiments, the inner spline 2106 may be electrically isolated from the outer tube 2104, and the distal geometry of the surgical tool 1600 may be configured as a tube within a tube, also electrically isolated. Consequently, monopolar energy may be delivered to the end effector 2110.

Figure 22:
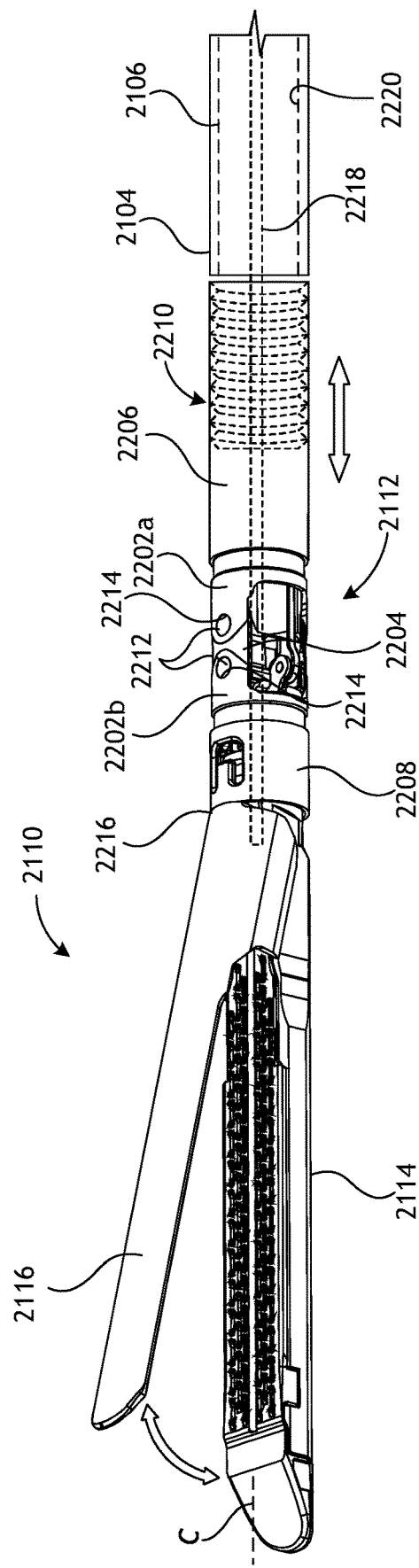
FIG. 22 is an enlarged isometric view of the end effector and the wrist of FIG. 21, according to one or more embodiments.

Referring now to FIG. 22, with continued reference to FIG. 21, depicted is an enlarged isometric view of the end effector 2110 and the wrist 2112, according to one or more embodiments. As illustrated, the wrist 2112 may include a first or "proximal" clevis 2202a, a second or "distal" clevis 2202b, and a closure link 2204 configured to operatively couple the proximal and distal devises 2202a,b across the wrist 2112. The proximal clevis 2202a may be coupled to or otherwise form part of the distal end of a closure tube 2206, and the distal clevis 2202b may be coupled to or otherwise form part of a closure ring 2208 arranged adjacent the jaws 2114, 2116.

In the illustrated embodiment, the inner spline 2106 (shown in dashed lines) extends distally within the outer tube 2104 toward the end effector 2110. At or near the end effector 2110, a distal end 2210 of the inner spline 2106 may be threadably engaged to the closure tube 2206 such that rotating the inner spline 2106 causes the closure tube 2206 to advance or retract longitudinally, as shown by the arrow D, and depending on the rotation direction of the inner spline 2106. Axial movement of the closure tube 2206 along the longitudinal axis C, as acted upon by the threaded engagement with the inner spline 2106 correspondingly moves the proximal clevis 2202a in the same axial direction.

The closure link 2204 may be configured to transmit an axial load through (across) the wrist 2112 to close the jaws 2114, 2116 of the end effector 2110. More specifically, the closure link 2204 defines a pair of pins 2012 configured to mate with corresponding apertures 2014 defined in each of the proximal and distal devises 2202a,b. The closure link 2204 may transmit the closure load or translation movement of the closure tube 2206 from the distal clevis 2202b to the proximal clevis 2202a and the closure ring 2208 will correspondingly push or pull on the upper jaw 2116 to close or open the upper jaw 2116. To close the upper jaw 2116, the closure ring 2208 is forced distally against a shoulder 2216 at or near the back of the upper jaw 2116, which urges the upper jaw 2116 to pivot down and to the closed position. To open the upper jaw 2116, the closure ring 2208 is retracted proximally away from the shoulder 2014 by retracting the closure tube 2206 through reverse rotation of the inner spline 2106. In some embodiments, proximal movement of the closure ring 2208 helps pull the upper jaw 2116 back toward the open position. In other embodiments, however, the upper jaw 2116 may be spring loaded and biased to the open position.

In some embodiments, an electrical conductor 2218 may extend distally to the end effector 2110 within a lumen 2220 defined by the inner spline 2106. In such embodiments, the electrical conductor 2218 may provide monopolar (or bipolar) electrical current to the jaws 2114, 2116 for electrocautery purposes.

4. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
   a handle;
   an elongate shaft including an outer proximal tube and an inner spline each extending through the handle, the inner spline being rotatably received within the outer proximal tube;
   a first actuation system housed within the handle and operable to rotate the inner spline relative to the outer proximal tube and thereby transfer torque to a proximal or distal end of the shaft; and
   a second actuation system housed within the handle and operable to drive the outer proximal tube and thereby advance or retract the elongate shaft in z-axis translation through the handle.

2. The robotic surgical tool of claim 1, wherein the outer proximal tube and the inner spline comprise a proximal shaft assembly and the shaft further includes a distal shaft assembly coupled to the proximal shaft assembly at a connector, the distal shaft assembly comprising:
   an outer distal tube extending distally from the connector;
   an inner distal tube arranged within the outer distal tube and extending distally from the connector; and
   a distal tip arranged at a distal end of the shaft and fixed to the outer and inner distal tubes,
   wherein the inner distal tube defines a first lumen and the inner spline defines a second lumen in fluid communication with the first lumen via the connector to enable fluid flow along a length of the shaft.

3. The robotic surgical tool of claim 2, wherein the outer proximal tube is fixed to the connector and the inner spline is rotatably coupled to the connector.

4. The robotic surgical tool of claim 2, wherein the connector provides a sealed interface between the first and second lumens.

5. The robotic surgical tool of claim 2, wherein the distal tip defines an opening in fluid communication with the first lumen to discharge fluids from the shaft or receive fluids into the shaft.

6. The robotic surgical tool of claim 2, further comprising a flow control system arranged at a proximal end of the shaft and including:

a valve operatively coupled to the inner spline such that rotation of the inner spline actuates the valve;
   a first conduit in fluid communication with the valve to convey a liquid into the first and second lumens to be discharged at the distal tip; and
   a second conduit in fluid communication with the valve to draw fluids into the first and second lumens at the distal tip.

7. The robotic surgical tool of claim 6, further comprising a third conduit in fluid communication with the valve to convey a compressed gas into the first and second lumens to be discharged at the distal tip.

8. The robotic surgical tool of claim 1, wherein the first actuation system includes a first drive input mounted to the handle and operable to actuate a first drive mechanism engageable with longitudinally-extending gear teeth defined on the inner spline to rotate the inner spline, and
   wherein the second actuation system includes a second drive input mounted to the handle and operable to actuate a second drive mechanism engageable with a rack provided on the outer proximal tube to advance or retract the shaft in z-axis translation.

9. The robotic surgical tool of claim 8, wherein the first actuation system includes a drive gear capable of sliding along the longitudinally-extending gear teeth as the shaft moves in z-axis translation.

10. The robotic surgical tool of claim 1, further comprising an end effector arranged at a distal end of the shaft, wherein the torque transferred by the inner spline causes actuation of the end effector.

11. The robotic surgical tool of claim 10, wherein the inner spline defines a lumen and the robotic surgical tool further comprises an electrical conductor extending within the lumen to the end effector.

12. The robotic surgical tool of claim 10, wherein the end effector includes opposing jaws and rotation of the inner spline moves the jaws between open and closed positions.

13. A method of operating a robotic surgical tool, comprising:
    arranging a robotic surgical tool adjacent a patient, the robotic surgical tool including an elongate shaft including an outer proximal tube and an inner spline each extending through a handle, the inner spline being rotatably received within the outer proximal tube;
    operating a first actuation system housed within the handle to rotate the inner spline relative to the outer proximal tube and thereby transferring torque to a proximal or distal end of the shaft; and
    operating a second actuation system housed within the handle to drive the outer proximal tube and thereby advance or retract the elongate shaft in z-axis translation through the handle.

14. The method of claim 13, wherein the outer proximal tube and the inner spline comprise a proximal shaft assembly and the shaft further includes a distal shaft assembly coupled to the proximal shaft assembly at a connector, the distal shaft assembly including:
    an outer distal tube extending distally from the connector;
    an inner distal tube arranged within the outer distal tube and extending distally from the connector; and
    a distal tip arranged at a distal end of the shaft and fixed to the outer and inner distal tubes, wherein the inner distal tube defines a first lumen and the inner spline defines a second lumen in fluid communication with the first lumen via the connector,
    the method further comprising flowing a fluid along a length of the shaft within the first and second lumens.

15. The method of claim 14, wherein the distal tip defines an opening in fluid communication with the first lumen, the method further comprising:
discharging the fluid from the shaft at the distal tip; and
drawing the fluid into the shaft at the distal tip.

16. The method of claim 14, wherein the robotic surgical tool further includes a flow control system arranged at a proximal end of the shaft and including a valve operatively coupled to the inner spline, and wherein operating the second actuation system further comprises:
actuating the valve to a first position and thereby conveying the fluid into the first and second lumens from to be discharged at the distal tip; and
actuating the valve to a second position and thereby drawing the fluid into the first and second lumens at the distal tip.

17. The method of claim 13, wherein operating the first actuation system comprises operating a first drive input mounted to the handle and thereby actuating a first drive mechanism to engage and drive longitudinally-extending gear teeth defined on the inner spline, and
wherein operating the second actuation system comprises operating a second drive input mounted to the handle and thereby actuating a second drive mechanism to engage and drive a rack provided on the outer proximal tube to advance or retract the shaft in z-axis translation.

18. The method of claim 17, wherein the first actuation system includes a drive gear engageable with the longitudinally-extending gear teeth, the method further comprising sliding the drive gear along the longitudinally-extending gear teeth as the shaft moves in z-axis translation.

19. The method of claim 13, wherein the robotic surgical tool further comprises an end effector arranged at a distal end of the shaft, and wherein operating the first actuation system comprises:
transferring the torque to the end effector via rotation of the inner spline; and actuating the end effector with the torque.

20. The method of claim 19, wherein the inner spline defines a lumen and the robotic surgical tool further includes an electrical conductor extending within the lumen to the end effector, the method further comprising providing electrical current to the end effector via the electrical conductor.

* * * * *